(12) United States Patent
Fischer et al.

(10) Patent No.: US 11,384,186 B2
(45) Date of Patent: *Jul. 12, 2022

(54) POLYMER COMPRISING CERTAIN LEVEL OF BIO-BASED CARBON

(71) Applicant: Clariant International Ltd., Muttenz (CH)

(72) Inventors: Dirk Fischer, Hahnheim (DE); Christoph Kayser, Mainz (DE); Gundula Starkulla, Mainz (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/468,641

(22) PCT Filed: Dec. 4, 2017

(86) PCT No.: PCT/EP2017/081415
§ 371 (c)(1),
(2) Date: Jun. 11, 2019

(87) PCT Pub. No.: WO2018/108609
PCT Pub. Date: Jun. 21, 2018

(65) Prior Publication Data
US 2020/0095356 A1 Mar. 26, 2020

(30) Foreign Application Priority Data

Dec. 12, 2016 (EP) .................................... 16203552

(51) Int. Cl.
| | | |
|---|---|---|
| C08F 220/58 | (2006.01) |
| A61Q 19/10 | (2006.01) |
| A61Q 1/02 | (2006.01) |
| A61Q 19/08 | (2006.01) |
| A61K 8/46 | (2006.01) |
| A61K 8/42 | (2006.01) |
| A61K 8/362 | (2006.01) |
| A61K 8/26 | (2006.01) |
| A61K 8/92 | (2006.01) |
| A61K 8/891 | (2006.01) |
| A61K 8/29 | (2006.01) |
| A61K 8/20 | (2006.01) |
| A61K 8/49 | (2006.01) |
| A61K 8/35 | (2006.01) |
| A61K 8/73 | (2006.01) |

(52) U.S. Cl.
CPC ............ *C08F 220/585* (2020.02); *A61K 8/20* (2013.01); *A61K 8/26* (2013.01); *A61K 8/29* (2013.01); *A61K 8/355* (2013.01); *A61K 8/362* (2013.01); *A61K 8/42* (2013.01); *A61K 8/463* (2013.01); *A61K 8/498* (2013.01); *A61K 8/735* (2013.01); *A61K 8/891* (2013.01); *A61K 8/922* (2013.01); *A61Q 1/02* (2013.01); *A61Q 19/08* (2013.01); *A61Q 19/10* (2013.01); *C08F 2800/10* (2013.01); *C08F 2810/20* (2013.01); *C08F 2810/50* (2013.01)

(58) Field of Classification Search
None
See application file for complete search history.

(56) References Cited

U.S. PATENT DOCUMENTS

| | | |
|---|---|---|
| 2,614,989 A | 10/1952 | Hunter |
| 2,809,971 A | 10/1957 | Bernstein |
| 2,865,876 A | 12/1958 | Scott, Jr. |
| 2,904,580 A | 9/1959 | Idol, Jr. |
| 2,905,565 A | 9/1959 | Dietz |
| 3,052,628 A | 9/1962 | Stanberry, Jr. |
| 3,236,733 A | 2/1966 | Karsten |
| 3,509,113 A | 4/1970 | Monagle |
| 3,544,597 A | 12/1970 | Killam |
| 3,753,196 A | 8/1973 | Kurtz |
| 3,761,418 A | 9/1973 | Parran |
| 3,937,721 A | 2/1976 | Schroeck |
| 3,960,918 A | 6/1976 | Schroeck |
| 4,015,991 A | 4/1977 | Persinski |
| 4,138,430 A | 2/1979 | Stiles |

(Continued)

FOREIGN PATENT DOCUMENTS

| | | |
|---|---|---|
| CN | 101066940 A | 11/2007 |
| CN | 101636381 A | 1/2010 |

(Continued)

OTHER PUBLICATIONS

Adhikary et al, Synthesis, characterization, and application of amylopectin-graft-poly(AM-co-AMPS), Journal of Applied Polymer Science (2012), 126(S1), 6 pages.

(Continued)

*Primary Examiner* — Dominic Lazaro
(74) *Attorney, Agent, or Firm* — Tod A. Waldrop

(57) ABSTRACT

The present invention relates to a polymer comprising: (a) from 90 mol-% to 99.9 mol-%, of repeating units according to Formula (1) wherein at least 10 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

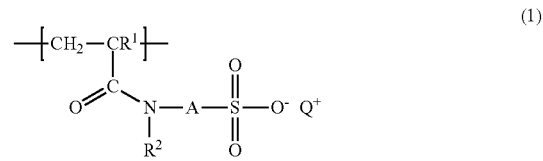

(1)

and (b) from 0.01 mol-% to 10 mol-% of crosslinking or branching units, wherein the crosslinking or branching units result from the incorporation of a monomer comprising at least two olefinically unsaturated double bonds.

20 Claims, 3 Drawing Sheets

(56) References Cited

U.S. PATENT DOCUMENTS

| | | |
|---|---|---|
| 4,323,683 A | 4/1982 | Bolich, Jr. |
| 4,342,653 A | 8/1982 | Halverson |
| 4,345,080 A | 8/1982 | Bolich, Jr. |
| 4,379,753 A | 4/1983 | Bolich, Jr. |
| 4,470,982 A | 9/1984 | Winkler |
| 4,487,864 A | 12/1984 | Bermudez |
| 4,555,269 A | 11/1985 | Rao |
| 4,655,943 A | 4/1987 | Elmquist |
| 4,669,920 A | 6/1987 | Dymond |
| 4,703,801 A | 11/1987 | Fry |
| 4,722,958 A | 2/1988 | Sauer |
| 4,800,071 A | 1/1989 | Kaesler |
| 4,931,489 A | 6/1990 | Kucera |
| 5,025,040 A | 6/1991 | Crema |
| 5,104,646 A | 4/1992 | Bolich, Jr. |
| 5,194,639 A | 3/1993 | Connor |
| 5,331,021 A | 7/1994 | Ahmed |
| 5,472,051 A | 12/1995 | Brothers |
| 5,510,049 A | 4/1996 | Connor |
| 5,792,828 A | 8/1998 | Quinn |
| 6,277,900 B1 | 8/2001 | Oswald |
| 6,297,337 B1 | 10/2001 | Marchant |
| 6,437,068 B2 | 8/2002 | Loeffler |
| 6,683,144 B2 | 1/2004 | Loeffler |
| 6,891,009 B2 | 5/2005 | Loeffler |
| 7,208,556 B2 | 4/2007 | Loeffler |
| 8,420,214 B2 | 4/2013 | Kavanagh |
| 8,629,224 B2 | 1/2014 | Loeffler |
| 9,399,692 B1 | 7/2016 | Jiang |
| 9,434,793 B1 | 9/2016 | Kane |
| 9,611,419 B1 | 4/2017 | Ferrell, Jr. |
| 11,142,494 B2 | 10/2021 | Kayser |
| 2003/0064044 A1 | 4/2003 | Chen |
| 2004/0228809 A1 | 11/2004 | Birkel |
| 2005/0003984 A1 | 1/2005 | Himmrich |
| 2006/0019835 A1 | 1/2006 | Kayser |
| 2007/0100102 A1 | 5/2007 | Fenchl |
| 2008/0226577 A1 | 9/2008 | L Alloret |
| 2010/0048850 A1 | 2/2010 | Dubois |
| 2010/0274048 A1 | 10/2010 | Wakayama |
| 2010/0278763 A1 | 11/2010 | Loeffler |
| 2010/0311904 A1 | 12/2010 | Chambers |
| 2010/0331904 A1 | 12/2010 | Warren |
| 2011/0110878 A1 | 5/2011 | Knappe |
| 2011/0136718 A1 | 6/2011 | Rodrigues |
| 2011/0318515 A1 | 12/2011 | Dubois |
| 2012/0039819 A1 | 2/2012 | Nakatani |
| 2012/0100084 A1 | 4/2012 | Peter |
| 2012/0138299 A1 | 6/2012 | Joseph |
| 2013/0043384 A1 | 2/2013 | Matsumoto |
| 2013/0129652 A1 | 5/2013 | Blin |
| 2014/0051819 A1 | 2/2014 | Davidson |
| 2014/0086854 A1* | 3/2014 | Klug .......... A61K 8/8158 424/59 |
| 2014/0127147 A1 | 5/2014 | Klug |
| 2014/0128513 A1 | 5/2014 | Carlson |
| 2014/0154758 A1 | 6/2014 | Dubois |
| 2014/0256880 A1 | 9/2014 | Rodrigues |
| 2015/0239803 A1 | 8/2015 | Sun |
| 2015/0329877 A1 | 11/2015 | Bockrath |
| 2016/0177002 A1 | 6/2016 | Palchik |
| 2016/0185948 A1 | 6/2016 | Kaneumi |
| 2016/0190641 A1 | 6/2016 | Lee |
| 2016/0194416 A1 | 7/2016 | Fukuhara |
| 2016/0194423 A1 | 7/2016 | Michitaka |
| 2016/0200670 A1 | 7/2016 | Reb |
| 2016/0200952 A1 | 7/2016 | Takahara |
| 2016/0211521 A1 | 7/2016 | Iwayasu |
| 2016/0214896 A1 | 7/2016 | Cadix |
| 2016/0222580 A1 | 8/2016 | Shimada |
| 2016/0236982 A1 | 8/2016 | Menceloglu |
| 2016/0244594 A1 | 8/2016 | Langlotz |
| 2016/0244629 A1 | 8/2016 | Xu |
| 2016/0271988 A1 | 9/2016 | Oharuda |
| 2016/0272676 A1 | 9/2016 | Kozlov |
| 2016/0288045 A1 | 10/2016 | Kramer |
| 2016/0298110 A1 | 10/2016 | McGall |
| 2016/0333199 A1 | 11/2016 | Akkerman |
| 2016/0333215 A1 | 11/2016 | Kawai |
| 2016/0340456 A1 | 11/2016 | Mori |
| 2016/0340540 A1 | 11/2016 | Brust |
| 2016/0340541 A1 | 11/2016 | Lele |
| 2016/0340617 A1 | 11/2016 | Orizet |
| 2016/0346188 A1 | 12/2016 | Singh |
| 2016/0346395 A1 | 12/2016 | Reineke |
| 2016/0354771 A1 | 12/2016 | Inomata |
| 2016/0355624 A1 | 12/2016 | Chen |
| 2016/0355735 A1 | 12/2016 | Motooka |
| 2016/0355736 A1 | 12/2016 | Motooka |
| 2016/0359156 A1 | 12/2016 | Ohkubo |
| 2016/0367468 A1 | 12/2016 | Graham |
| 2016/0369025 A1 | 12/2016 | Yukawa |
| 2017/0001188 A1 | 1/2017 | Choi |
| 2017/0001382 A1 | 1/2017 | Stepper |
| 2017/0002152 A1 | 1/2017 | Fonnum |
| 2017/0009111 A1 | 1/2017 | Bauer |
| 2017/0015693 A1 | 1/2017 | Carlson |
| 2017/0022451 A1 | 1/2017 | Tamareselvy |
| 2017/0029305 A1 | 2/2017 | Gill |
| 2017/0029548 A1 | 2/2017 | Kawai |
| 2017/0030015 A1 | 2/2017 | Amin |
| 2017/0031243 A1 | 2/2017 | Hatakeyama |
| 2017/0037170 A1 | 2/2017 | Gonzalez |
| 2017/0037206 A1 | 2/2017 | Antheunis |
| 2017/0037286 A1 | 2/2017 | Lee |
| 2017/0038500 A1 | 2/2017 | Benz |
| 2017/0044287 A1 | 2/2017 | Yahagi |
| 2017/0045819 A1 | 2/2017 | Karasawa |
| 2017/0059990 A1 | 3/2017 | Tsuchimura |
| 2017/0073446 A1 | 3/2017 | Corten |
| 2017/0106013 A1 | 4/2017 | Piergallini |
| 2017/0121567 A1 | 5/2017 | Kawasaki |
| 2017/0123106 A1 | 5/2017 | Chien |
| 2017/0123229 A1 | 5/2017 | Chien |
| 2017/0129812 A1 | 5/2017 | Langlotz |
| 2017/0130076 A1 | 5/2017 | Most |
| 2017/0135941 A1 | 5/2017 | Green |
| 2017/0145244 A1 | 5/2017 | Yang |
| 2017/0158951 A1 | 6/2017 | Liang |
| 2017/0166776 A1 | 6/2017 | Derocher |
| 2017/0174901 A1 | 6/2017 | Okumura |
| 2017/0174905 A1 | 6/2017 | Bohling |
| 2017/0175335 A1 | 6/2017 | Daniels |
| 2017/0198189 A1 | 7/2017 | Panamarathupalayam |
| 2017/0210864 A1 | 7/2017 | Zhao |
| 2017/0210937 A1 | 7/2017 | Okazaki |
| 2017/0214047 A1 | 7/2017 | Naito |
| 2017/0225404 A1 | 8/2017 | Naruse |
| 2017/0226050 A1 | 8/2017 | Voronov |
| 2017/0240799 A1 | 8/2017 | Wei |
| 2017/0242174 A1 | 8/2017 | Ito |
| 2017/0244095 A1 | 8/2017 | Sonobe |
| 2017/0247487 A1 | 8/2017 | Hemmi |
| 2017/0247489 A1 | 8/2017 | Tekobo |
| 2017/0253683 A1 | 9/2017 | Fujiwara |
| 2017/0275408 A1 | 9/2017 | Yang |
| 2017/0275447 A1 | 9/2017 | Junk |
| 2017/0275813 A1 | 9/2017 | Isobe |
| 2017/0283537 A1 | 10/2017 | Hatton |
| 2017/0291971 A1 | 10/2017 | Serrano |
| 2017/0298155 A1 | 10/2017 | Takafuji |
| 2017/0299779 A1 | 10/2017 | Mita |
| 2017/0305855 A1 | 10/2017 | Klun |
| 2017/0306060 A1 | 10/2017 | Fujita |
| 2017/0306195 A1 | 10/2017 | Lachapell |
| 2017/0313801 A1 | 11/2017 | Takeo |
| 2017/0320985 A1 | 11/2017 | Al-Ghamdi |
| 2017/0321050 A1 | 11/2017 | Elanany |
| 2017/0327679 A1 | 11/2017 | Ghosh |
| 2017/0334778 A1 | 11/2017 | Vilinska |
| 2017/0342220 A1 | 11/2017 | Iijima |
| 2017/0348219 A1 | 12/2017 | Uyama |
| 2017/0349679 A1 | 12/2017 | Yashiki |
| 2017/0355873 A1 | 12/2017 | Wu |

(56) References Cited

U.S. PATENT DOCUMENTS

| | | |
|---|---|---|
| 2017/0361297 A1 | 12/2017 | Yamanaka |
| 2017/0363956 A1 | 12/2017 | Mizuguchi |
| 2017/0369697 A1 | 12/2017 | Yahagi |
| 2017/0369698 A1 | 12/2017 | Suzuki |
| 2018/0002553 A1 | 1/2018 | Harada |
| 2018/0002563 A1 | 1/2018 | Taylor |
| 2018/0008936 A1 | 1/2018 | Martinez |
| 2018/0016739 A1 | 1/2018 | Coppens |
| 2018/0036689 A1 | 2/2018 | Inoue |
| 2018/0037753 A1 | 2/2018 | Dombrowski |
| 2018/0052152 A1 | 2/2018 | Sacha |
| 2018/0057629 A1 | 3/2018 | Letondor |
| 2018/0072932 A1 | 3/2018 | Kaneko |
| 2018/0079158 A1 | 3/2018 | Qiu |
| 2018/0080119 A1 | 3/2018 | Strand |
| 2018/0086936 A1 | 3/2018 | Steiner |
| 2018/0086966 A1 | 3/2018 | Favero |
| 2018/0093113 A1 | 4/2018 | Schade |
| 2018/0111900 A1 | 4/2018 | Miller |
| 2018/0118970 A1 | 5/2018 | Kaur |
| 2018/0118978 A1 | 5/2018 | Yabu |
| 2018/0133662 A1 | 5/2018 | Kang |
| 2018/0133986 A1 | 5/2018 | Harada |
| 2018/0148578 A1 | 5/2018 | Ohta |
| 2018/0148635 A1 | 5/2018 | Shen |
| 2018/0155478 A1 | 6/2018 | Kayser |
| 2018/0163078 A1 | 6/2018 | Sukhishvili |
| 2018/0169296 A1 | 6/2018 | Benz |
| 2018/0171051 A1 | 6/2018 | Junk |
| 2018/0171203 A1 | 6/2018 | Cadix |
| 2018/0171207 A1 | 6/2018 | Fischer |
| 2018/0171208 A1 | 6/2018 | Fischer |
| 2018/0179412 A1 | 6/2018 | Bitler |
| 2018/0186993 A1 | 7/2018 | Tanida |
| 2018/0194882 A1 | 7/2018 | Chambrol |
| 2018/0194948 A1 | 7/2018 | Fan |
| 2018/0194969 A1 | 7/2018 | An |
| 2018/0201713 A1 | 7/2018 | Iwasaki |
| 2018/0206484 A1 | 7/2018 | Bittner |
| 2018/0215925 A1 | 8/2018 | Hatanaka |
| 2018/0217294 A1 | 8/2018 | Hyuugaji |
| 2018/0229023 A1 | 8/2018 | Hatakeyama |
| 2018/0229024 A1 | 8/2018 | Hatakeyama |
| 2018/0230256 A1 | 8/2018 | Yamamuro |
| 2018/0237561 A1 | 8/2018 | Hatakeyama |
| 2018/0237567 A1 | 8/2018 | Klee |
| 2018/0240564 A1 | 8/2018 | Hatakeyama |
| 2018/0244609 A1 | 8/2018 | Favero |
| 2018/0244911 A1 | 8/2018 | Iso |
| 2018/0258297 A1 | 9/2018 | Kitou |
| 2018/0273743 A1 | 9/2018 | Sumerlin |
| 2018/0273761 A1 | 9/2018 | Yoshimura |
| 2018/0273774 A1 | 9/2018 | Brown |
| 2018/0290377 A1 | 10/2018 | Talken |
| 2018/0291219 A1 | 10/2018 | Kiyosada |
| 2018/0312739 A1 | 11/2018 | Panamarathupalayam |
| 2018/0321589 A1 | 11/2018 | Tsuchimura |
| 2018/0325789 A1 | 11/2018 | Takemoto |
| 2018/0327585 A1 | 11/2018 | Adkins |
| 2018/0340098 A1 | 11/2018 | Tanabe |
| 2018/0344615 A1 | 12/2018 | Gamez-Garcia |
| 2018/0346626 A1 | 12/2018 | Ying |
| 2018/0346634 A1 | 12/2018 | Rodriguez-Emmenegger |
| 2018/0346804 A1 | 12/2018 | Blazewicz |
| 2018/0348405 A1 | 12/2018 | Chien |
| 2018/0351149 A1 | 12/2018 | Akiike |
| 2018/0353650 A1 | 12/2018 | Bose |
| 2018/0356561 A1 | 12/2018 | Hyugaji |
| 2018/0362689 A1 | 12/2018 | Jimenez Garcia |
| 2018/0362833 A1 | 12/2018 | Jackson |
| 2019/0058195 A1 | 2/2019 | Hanasaki |
| 2019/0202737 A1 | 7/2019 | Hesselbarth |
| 2019/0241509 A1 | 8/2019 | Kayser |
| 2019/0338060 A1 | 11/2019 | Fischer |
| 2019/0359735 A1 | 11/2019 | Fischer |
| 2020/0009041 A1 | 1/2020 | Fischer |
| 2020/0010598 A1 | 1/2020 | Fischer |
| 2020/0017618 A1 | 1/2020 | Fischer |
| 2020/0017619 A1 | 1/2020 | Fischer |
| 2020/0078287 A1 | 3/2020 | Fischer |
| 2020/0095356 A1 | 3/2020 | Fischer |
| 2020/0270506 A1 | 8/2020 | Fischer |

FOREIGN PATENT DOCUMENTS

| | | |
|---|---|---|
| CN | 102351744 A | 2/2012 |
| CN | 102361894 A | 2/2012 |
| CN | 102952044 A | 3/2013 |
| CN | 103492437 A | 1/2014 |
| CN | 103819614 | 5/2014 |
| CN | 104204080 A | 12/2014 |
| CN | 104884628 A | 9/2015 |
| CN | 105694403 A | 6/2016 |
| DE | 2655891 | 6/1977 |
| EP | 0116671 | 8/1984 |
| EP | 0157055 | 10/1985 |
| EP | 0217608 | 4/1987 |
| EP | 0244981 | 11/1987 |
| EP | 0550637 | 7/1993 |
| EP | 0750899 | 1/1997 |
| EP | 0816403 | 1/1998 |
| EP | 1045869 | 10/2000 |
| EP | 1084696 | 3/2001 |
| EP | 1351654 A1 | 10/2003 |
| EP | 2105127 | 9/2009 |
| EP | 2166060 | 3/2010 |
| JP | 2008084852 A | 4/2008 |
| JP | 2009149536 A | 7/2009 |
| JP | 2010519191 A | 6/2010 |
| JP | 2011506703 A | 3/2011 |
| JP | 2012087256 A | 5/2012 |
| JP | 2012521448 A | 9/2012 |
| JP | 2014500334 | 1/2014 |
| JP | 2014055232 A | 3/2014 |
| JP | 2014511423 A | 5/2014 |
| WO | 9206154 | 4/1992 |
| WO | 9507340 | 3/1995 |
| WO | 9800094 | 1/1998 |
| WO | 9924549 | 5/1999 |
| WO | 9926991 | 6/1999 |
| WO | 9966017 | 12/1999 |
| WO | 0226925 | 4/2002 |
| WO | 2009063120 A1 | 5/2009 |
| WO | 2009072480 A | 6/2009 |
| WO | 2010092875 A1 | 8/2010 |
| WO | 2011089709 | 7/2011 |
| WO | 2012084977 A1 | 6/2012 |
| WO | 2012113671 | 8/2012 |
| WO | 2013017262 | 2/2013 |
| WO | 2013113938 A1 | 8/2013 |
| WO | 2013120636 A1 | 8/2013 |
| WO | 2013178668 | 12/2013 |
| WO | 2013178700 | 12/2013 |
| WO | 2014004616 | 1/2014 |
| WO | 2014086780 | 6/2014 |
| WO | 2014088034 | 6/2014 |
| WO | 2015034948 | 3/2015 |
| WO | 2016042011 | 3/2016 |
| WO | 2017220512 | 12/2017 |

OTHER PUBLICATIONS

Anonymous, "Bio-based material—Wikipedia, the free encyclopedia", (Mar. 12, 2015), URL: https://en.wikipedia.org/wiki/Bio-based_material, (Sep. 1, 2016), XP055299147.

ASTM International, ASTM D6866-12, Standard Test Methods for Determining the Biobased Content of Solid, Liquid, and Gaseous Samples Using Radiocarbon Analysis (2012) (Year: 2012).

Babu, R. P. et al., "Current progress on bio-based polymers and their future trends", Progress in Biomaterials 2013, 2(8), 1-16. (Year: 2013).

Bernd Tieke, "Makromolekulare Chemie Chapter 3", ISBN 10:3527313796, 2005.

(56) References Cited

OTHER PUBLICATIONS

Bernd Tieke, "Makromolekulare Chemie: Eine Einführung", Wiley-VCH, 2. vollständig überarbeitete und erweiterte Auflage (3. Nachdruck 2010) ISBN-13: 978 3-527-31379-2, p. 259-261.
Bianca et al., "Fermentative production of isobutene", Appl Microbiol Biotechnol (2012) 93:1377-1387.
CTFA Cosmetic Ingredient Dictionary, Second Edition, 1977, 3 pages.
CTFA Cosmetic Ingredient Handbook, Second Edition, 1992, 2 pages.
De Jong et al., "Product developments in the bio-based chemicals arena", Biofuels, Bioprod. Bioref. 6:606-624 (2012).
Dräger-Röhrchen & CMS—Handbuch, 17. Auflage, Mar. 2015, 9 pages.
EP1351654B1—Google English Translation (Year: 2003), 19 pages.
George Odian, "Principles of Polymerization", Third Edition, Wiley-Interscience, New York, in chapter 1-4, p. 19 to 24, ISBN 0-471-61020-8, Aug. 1992.
International Cosmetic Ingredient Dictionary, Fifth Edition, 1993.
International Preliminary Report on Patentability for PCT/EP2017/064977, dated Dec. 25, 2018, 7 pages.
International Search Report for App. No. PCT/EP2017/081415, dated Jan. 16, 2018, 3 pages.
International Search Report for App. No. PCT/EP2017/081417, dated Apr. 4, 2018, 2 pages.
International Search Report for App. No. PCT/EP2017/081667, dated Jan. 23, 2018, 3 pages.
International Search Report for App. No. PCT/EP2017/081681, dated Apr. 11, 2018, 3 pages.
International Search Report for PCT/EP2017/06477, dated Aug. 29, 2017, 2 pages.
International Search Report for PCT/EP2017/081665, dated Jan. 23, 2018, 2 pages.
International Search Report for PCT/EP2017/081666, dated Jan. 23, 2018, 2 pages.
Kourosh Kabiri et al: "Chitosan-modified nanoclay-poly(AMPS) nanocomposite hydrogels with improved gel strength", Polymer International, vol. 58, No. 11, Sep. 10, 2009 (Sep. 10, 2009), pp. 1252-1259, XP055379190.
Le Notre et al, Green Chemistry, Biobased synthesis of acrylonitrile from glutamic acid, 2011,13, pp. 807-809, (Year: 2011).
Le Notre et al., "Supporting Information, Biobased synthesis of acrylonitrile from glutamic acid", Green Chemistry, 2011, 13(4), pp. 807-809.
M. A. Bañares, M. O. Guerrero-Pérez, "Appl. Catal. B: Environmental", 148-149 (2013) 601-603.
M. O. Guerrero-Pérez, M. A. Bañares, "New Reaction: Conversion of Glycerol into Acrylonitrile", ChemSusChem 1 (2008) 511-513.
M. O. Guerrero-Péreza and M. A. Bañares, "Metrics of acrylonitrile: From biomass vs. petrochemical route", Catalysis Today 239 (2015) 25-30.
Machine Translation of AOI Keigo, et al, Bio-based Polymers Seni Gakkaishi, 2010, vol. 66 No. 4, p. 124-128.
Machine Translation of Netsu Sokutei, 2012, 39(4), p. 143-150.
Masao Kunioka, "Measurement Methods of Biobased Carbon Content for Biomass-Based Chemicals and Plastics", Radioisotopes, 62, 901-925 (2013).
Mithilesh Yadav et al: "Superabsorbent nanocomposite (alginate-g-PAMPS/MMT): Synthesis, characterization and swelling behavior", Carbohydrate Polymers, Applied Science Publishers, Ltd. Barking, GB, vol. 90, No. 1, May 4, 2012 (May 4, 2012), pp. 165-173, XP028432003.
Pourjavadi et al, "Modified Carrageenan. 4. Synthesis and Swelling Behavior of Crosslinked KC-g-AMPS Superabsorbent Hydrogel with Antisalt and pH-Responsiveness Properties", Journal of Applied Polymer Science, vol. 98, 255-263 (2005).
Rana, V. et al, "Carbohydrate Polymers", 83 (2011) 1031-1047.
Renae Canterbery Pepe et al., International Cosmetic Ingredient Dictionary and Handbook, 9th Edition, 2002, vol. 4, Published by The Cosmetic, Toiletry, and Fragrance Association, 3 pages.
Srivastava et al, "Graft copolymerization of 2-Acrylamideo-2-methyl-1-propane sulphonic acid onto xanthan gum by ascorbic/bromate redox pair," PMSE Preprints (2004), 90, pp. 291-292.
Srivastava et al, Modification of natural polymer via free radical graft copolymerization of 2 acrylamideo-2-methyl-1-propane sulfonic acid in aqueous media and study of swelling and metal ion sorption behaviour, Journal of Applied Polymer Science (2009), 114(3), 1426-1434.
Tateo, F. et al. "Determination of gamma-butyrolactone (GBL) in foods by SBSE-TD/GC/MS". Journal of Food Composition and Analysis 2003, 16, 721-727. (Year: 2003).
Teodorescu, M. et al. "Poly(vinylpyrrolidone)—A Versatile Polymer for Biomedical and Beyond Medical Applications". Polymer-Plastics Technology and Engineering 2015, 54(9), pp. 923-943.
Zhang, Q. et al. "Enhancing the Acetylene Yield from Methane by Decoupling Oxidation and Pyrolysis Reactions: A Comparison with the Partial Oxidation Process". Industrial & Engineering Chemistry Research 2016, 55, 8383-8394 (Year: 2016).

\* cited by examiner

POLYMER COMPRISING CERTAIN LEVEL OF BIO-BASED CARBON

FIELD OF THE INVENTION

The present invention relates to a polymer having a certain bio-based carbon content obtained by polymerization, in addition to processes and uses in cosmetic applications.

BACKGROUND OF THE INVENTION

Cleansing and caring for the skin, scalp, and hair is very important for general hygiene e.g. for removal of unwanted materials such as sebum, oils, dirt, makeup, or for moisturisation, colouring or protection. Many cosmetic products require a certain minimum viscosity in order to achieve ease of application to the substrate and/or retention on the substrate to be treated. Many cosmetic products comprise viscosity-increasing or rheology-influencing agents. These are often referred to as thickening agents, thickeners or gelling agents. Thickening agents used in cosmetics or personal hygiene products include viscous liquids such as polyethylene glycol, synthetic polymers such as polyacrylic acid and vegetable gums. In the 1990s, innovative thickeners based on 2-acrylamido-2-methyl-1-propanesulfonic acid (AMPS) and their salts were introduced into the market (EP0816403 and WO98/00094). In both homopolymer and copolymer form (e.g. Aristoflex® AVC from Clariant), such thickeners are superior in many respects to the corresponding polycarboxylates (Carbopols).

Many materials employed for use as thickeners or rheology modifiers are traditionally derived from crude oil. Environmental, economic and sustainability questions are restricting the use of products derived from this limited resource: synthetic surfactants, for example, have been blamed for environmental incidents, particularly vis-à-vis aquatic problems in rivers and lakes. Therefore, there is a desire to identify more sustainable and biodegradable, yet gentle and effective materials. Indeed, consumers are very interested in "natural" products including products with a high percentage of "natural" compounds and/or compounds that are derived from renewable materials. Consumers perceive compounds derived from natural materials to be gentler and more environmentally friendly. Recent industrial developments in "bio-based" chemicals are summarised, for example, in de Jong et al, "Product developments in the bio-based chemicals arena", Biofuels, Bioprod. Bioref. 6:606-624 (2012).

Compounds derived from natural materials have various other benefits, including increased biodegradability and also more sustainable availability because they are not based on a limited resource. Compounds derived from plant-based resources are particularly useful since the source compound can simply be regrown. Consumers are also particularly comfortable with using compounds derived from well-known plants, especially those that are considered staple products.

Recently, classical monomers such as ethylene, acrylic acid or methyl methacrylate have been disclosed as being produced with renewable raw materials. US2014/0154758 (Arkema) discloses the preparation of methyl methacrylate wherein the method comprises the use of acetone cyanohydrin as a raw material, said acetone cyanohydrin being obtained by condensing cyanohydric acid in acetone, and the methyl methacrylate is prepared using a process involving the addition of methanol. Acetone and methanol can be sourced from renewable feedstock. DE 2655891 (DU PONT) discloses the oxidation from 1-propanol to acrylates. U.S. Pat. No. 4,138,430 (DU PONT) discloses the ammoxidation of 1-propanol to form acrylonitrile.

Different synthetic routes for the synthesis of bio-based acrylonitrile are described by M. Olga Guerrero-Péreza and Miguel A. Bañares in Catalysis Today 239 (2015) 25-30. The process for the direct production of acrylonitrile from glycerol was described recently by M. O. Guerrero-Pérez, M. A. Bañares, ChemSusChem 1 (2008) 511 and by M. A. Bañares, M. O. Guerrero-Pérez, Appl. Catal. B (2013), as well as in US20100048850A1 (Arkema) and WO2009063120A1 (CONSEJO SUPERIOR DE INVESTIGACIONES CIENTÍFICAS).

Bio-based propylene can directly been used in the so-called SOHIO process to form acrylonitrile. U.S. Pat. No. 2,904,580 (STANDARD OIL CO) describes the ammoxidation of propylene according to the so-called SOHIO process.

WO2014086780 (Global Bioenergies) discloses a fermentation method for several olefins including propene and isobutene. As seen before propene can be used as a raw material for the ammoxidation to acrylonitrile. Isobutene is an important raw material for polyisobutene rubbers and other downstream products such as tert.-butanol, iso-octanol, branched alkanes or branched alcohols.

WO2016/042011 (Global Bioenergies) describes an enzymatic method for the production of isobutene from 3-methylcrotonyl-CoA. WO2014/004616 (Gevo Inc) discloses the synthesis of isobutanol by recombinant yeast microorganisms. The catalytic dehydration leads to isobutene.

WO2015/034948 (MYRIANT CORP) describes the synthesis of bio-based acrylic acid by dehydration of 1.3-propandiol and subsequent oxidation of the allylic alcohol.

Nevertheless, the availability of more renewable polymers suitable for use as thickening agents is highly limited. Furthermore, there is a need for thickening agents that are not only more renewable, but also provide excellent performance. There is a need, therefore, for providing polymers that can provide the excellent performance of modern polymers yet from more sustainable sources.

SUMMARY OF THE INVENTION

In a first aspect, the present invention relates to a polymer comprising:
(a) from 90 mol-% to 99.9 mol-%, preferably from 95 mol-% to 99.5 mol-% of repeating units according to Formula (1) wherein at least 10%, preferably at least 20 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

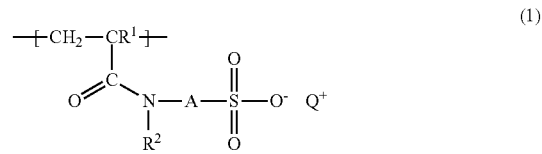

wherein:
$R^1$ and $R^2$ are independently selected from H, methyl or ethyl; A is a linear or branched $C_1$-$C_{12}$-alkyl group; and Q+ is H+, NH$_4$+, organic ammonium ions [NHR$^5$R$^6$R$^7$]+ wherein R$^5$, R$^6$, and R$^7$ independently of one another may be hydrogen, a linear or branched alkyl group having 1 to 22 carbon atoms, a linear or branched, singularly or multiply unsaturated alkenyl group having 2 to 22 carbon atoms, a C$_6$-C$_{22}$ alkylamidopropyl group, a linear mono-hydroxyalkyl group having 2 to carbon atoms or a linear or branched dihydroxyalkyl group having 3 to carbon atoms, and where at least one of the radicals R$^5$, R$^6$, and R$^7$ is not hydrogen, or Q+ is Li+, Na+, K+, ½ Ca++, ½ Mg++, ½ Zn++, ⅓ Al+++, or combinations thereof;

(b) from 0.01 mol-% to 10 mol-%, preferably from 0.01 mol-% to 5 mol-% of crosslinking or branching units, wherein the crosslinking or branching units result from the incorporation of a monomer comprising at least two olefinically unsaturated double bonds.

Other aspects relate to compositions, methods, uses, and processes related to the polymer disclosed in the first aspect.

DETAILED DESCRIPTION OF THE INVENTION

Definitions and General

Figure 1:
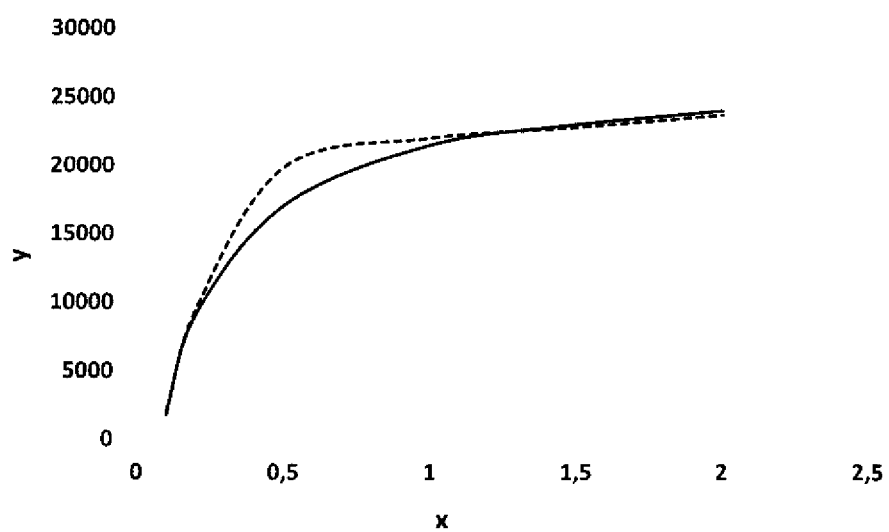
FIG. 1: Viscosity dependence on polymer concentration; measured in deionized water (Brookfield RVDV-1, 20° C., 20 rpm). The x-axis shows the concentration of polymer in wt.-%. The y-axis shows the viscosity in mPa·s. Polymer-B 16 (according to the invention; solid line) and a comparative polymer-B 16 # are compared (broken line).

In this document, including in all embodiments of all aspects of the present invention, the following definitions apply unless specifically stated otherwise. All percentages are by weight (w/w) of the total composition. "wt.-%" means percentage by weight; "vol.-%" means percentage by volume; "mol-%" means percentage by mole. All ratios are weight ratios. References to 'parts' e.g. a mixture of 1 part X and 3 parts Y, is a ratio by weight. "QS" or "QSP" means sufficient quantity for 100% or for 100 g.+/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein "min" means "minute" or "minutes". Herein "mol" means mole. Herein "g" following a number means "gram" or "grams". "Ex." means "example". All amounts as they pertain to listed ingredients are based on the active level ('solids') and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol and no other fatty alcohol, would fall within this scope.

The following acronyms are used herein: ACDMT=acryloyldimethyltaurate; AM=acrylamide; AN=acrylonitrile; tBAM=tert.-butyl acrylamide; IBSA=isobutene sulfonic acid; IBDSA=2-methylidene-1,3-propylenedisulfonic acid.

Unless otherwise stated, "viscosity" herein is measured at 20° C. viscosity in centipoise (cP) or mPa·s using a Brookfield viscometer model LV, RVT DV-II or LVT DV-II with 10-90% torque at 20 rpm.

"Molecular weight" or "M.Wt." "Mw", "M$_w$" or "MW" and grammatical equivalents mean the weight average molecular weight, unless otherwise stated. Also relevant for the determination of the molecular weight distribution is the number average molecular weight "Mn", "M$_n$" and grammatical equivalents, and the polydispersity "Ð" or "PDI".

Number Average Molecular Weight: Mn

The number average molecular weight is the statistical average molecular weight of all the polymer chains in the sample, and is defined by:

$$Mn = \frac{\sum NiMi}{\sum Ni}$$

where M$_i$ is the molecular weight of a chain and N$_i$ is the number of chains of that molecular weight. M$_n$ can be predicted by polymerisation mechanisms and is measured by methods that determine the number of molecules in a sample of a given weight; for example, colligative methods such as end-group assay. If M$_n$ is quoted for a molecular weight distribution, there are equal numbers of molecules on either side of M$_n$ in the distribution.

Weight Average Molecular Weight: M$_W$

The weight average molecular weight is defined by:

$$MW = \frac{\sum NiMi^2}{\sum NiMi}$$

Compared to $M_n$, $M_W$ takes into account the molecular weight of a chain in determining contributions to the molecular weight average. The more massive the chain, the more the chain contributes to $M_W$. $M_W$ is determined by methods that are sensitive to the molecular size rather than just their number, such as light scattering techniques. If $M_W$ is quoted for the molecular weight distribution, there is an equal weight of molecules on either side of $M_W$ in the distribution.

The polydispersity index PDI is used as a measure of the broadness of a molecular weight distribution of a polymer, and is defined by:

$$PDI = \frac{MW}{Mn}$$

The larger the PDI, the broader the molecular weight. A monodisperse polymer where all the chain lengths are equal (such as a protein) has an $M_W/M_n=1$.

The weight average molecular weight can be measured by gel permeation chromatography (GPC), also referred to as size exclusion chromatography (SEC). The molecular weight of polymers and its measurement is described in the textbook "Principles of Polymerization" by Georg Odian, third edition, Wiley-Interscience, New York, in chapter 1-4, page 19 to 24, ISBN 0-471-61020-8. The process to determine the weight average molecular weight is described in detail in chapter 3 of Makromolekulare Chemie: Eine Einführung" by Bernd Tieke, Wiley-VCH, 2. vollständig überarbeitete und erweiterte Auflage (3. Nachdruck 2010) ISBN-13: 978-3-527-31379-2, page 259-261.

Determination of molecular weight and distribution of samples by GPC is determined under the following conditions.
Column: PSS Suprema 30,000 Å 10 μm, 300 mm×8 mm
Detector: RID
Oven temperature: 23° C.
Flow: 1 ml/min
Injection volume: 20 μl
Eluent: 0.07 mol/l disodium hydrogen phosphate in water
Calibration method: Conventional poly(styrene sulfonate) sodium salt calibration Sample preparation: Weigh approx. 10 mg sample in 10 ml 0.07 mol/l disodium hydrogen phosphate in water and shake for 15 min.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Substantially free from" or "substantially free of" means less than 1%, or less than 0.8%, or less than 0.5%, or less than 0.3%, or about 0%, by total weight of the composition or formulation.

"Monomer" means a discrete, non-polymerised chemical moiety capable of undergoing polymerisation in the presence of an initiator or any suitable reaction that creates a macromolecule e.g. such as radical polymerisation, polycondensation, polyaddition, anionic or cationic polymerization, ring opening polymerisation or coordination insertion polymerisation. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Fuming sulfuric acid" herein means a solution of sulfur trioxide in sulfuric acid. Fuming sulfuric acid is also known as oleum and is identified by the CAS number 8014-95-7, and can be described by the formula $H_2SO_4.xSO_3$ where x is the molar free sulfur trioxide content.

The "biobased content" is reported in ASTM D6866-12, Method B (see section 3.3.9 of ASTM D6866-12). "Biobased carbon content", "biobased content", "biogenic carbon content", "bio-based content", "biomass-derived carbon" herein refer to the same thing and are all measured in wt.-%. Herein, the term 'bio-based carbon content' is used. ASTM D6866-12, Method B lab results report the percentage of bio-based carbon content relative to total carbon, and not to total mass of the sample or molecular weight. A comment on bio-based carbon content calculation: Presently ASTM D6866-12, Method B (see section 9 of ASTM D6866-12) requires the percent modern carbon value (pMC) reported to be multiplied by a correction factor of 0.95 to account for excess carbon-14 in the atmosphere due to nuclear weapons testing. However, a revision is pending for ASTM D6866-12, Method B to update the correction factor to 0.98 due to ongoing decrease in excess atmospheric $^{14}CO_2$. For the purposes of accuracy, the new correction factor of 0.98 is often reported in the field e.g. by suppliers. Generally, results below ~20% bio-based carbon will not be affected. However, results close to 100% will be ~2-3% bio-based carbon higher using the 0.98 factor vs 0.95. Results between ~20-90% will increase by 0-3%. Hence the term "bio-based carbon content" as used herein is defined by the equation:

Bio-based carbon content=$pMC*0.95(\%)$

A review on measurement methods of bio-based carbon content for biomass-based chemicals and plastics is given by Massao Kunioka in *Radioisotopes*, 62, 901-925 (2013).

"Hair" means mammalian keratin fibres including scalp hair, facial hair and body hair. It includes such hair still being attached to a living subject and also hair that has been removed therefrom such as hair swatches and hair on a doll/mannequin. In at least one embodiment, "hair" means human hair. "Hair shaft" or "hair fibre" means an individual hair strand and may be used interchangeably with the term "hair."

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salts and/or alcohol derivatives of a given compound. In at least one embodiment, "derivatives thereof" means the amide, ether, ester, amino, carboxyl, acetyl, acid, salt and alcohol derivatives.

Explanation of and Benefits Provided by the Invention

Surprisingly, it has now been found that it is possible to synthesise good quality bio-based ACDMT (see Formula (3) below) at acceptable yields.

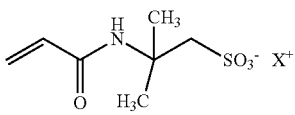

(3)

Indeed, when considering genetically-engineered microbes for use in creating bio-based ACDMT, currently no such microbes are commercially available. ACDMT itself is not similar to any other products that typical microbes would produce naturally. Furthermore, there are few natural microbial pathways capable of converting sulfonic acid groups. Therefore, the person skilled in the art naturally has a bias in his mind that it would be difficult to produce bio-based ACDMT in view of its more synthetic-type chemical moieties. The person skilled in the art, may however, consider that the reaction of acrylic acid with taurine, as bio-based materials could form the corresponding acryl-amido taurate compound, which is a similar structure as compared to ACDMT. However, the reactants would preferentiality react to form a Michael adduct, rather than an acryl-amido taurate compound. Hence, it would be known to the person skilled in the art that synthesising bio-based ACDMT is no trivial matter.

Bianca et al (Appl Microbiol Biotechnol (2012) 93:1377-1387) states that a high level of impurities are produced when bio-based isobutene is synthesised (⅔ carbon dioxide). WO2014086780A2 on pages 5 and 6 mentions various by-products and impurities that may result from the bio-based isobutene is synthesised. Indeed, on page 14 of WO2014086780A2 it states "The fermentation off-gas (i.e. a gas stream originating from the fermenter) typically comprises the hydrocarbon as the desired product and the intermediate together with additional gaseous components. Generally, the total content of the desired product, such as isobutene, and the intermediate, such as acetone, in the fermentation off-gas is in a range of 3 to 30 vol. %, preferably 3 to 20 vol. %". In other words, it is known in the art that a very low yield results when known bio-based isobutene synthesis processes are employed, as well as that a significant level of by-products is produced. Indeed, normally at least 98%, typically at least 99.5% purity of isobutene is used in conventional synthesis techniques. Surprisingly, it is possible to produce bio-based ACDMT despite using bio-based components that are typically impure in view of the microbes that produce the bio-based component creating by-products as a result of their natural enzymatic action. European patent application 16175218.3 filed on 20 Jun. 2016 in the name of Clariant International Ltd, the disclosure of which is incorporated herein by reference, discloses the synthesis of bio-based acryloyldimethyltaurate, which can be used as a monomer for the polymer according to the present invention.

Furthermore it has surprisingly been found that polymers containing such novel bio-based components can be synthesised. Such polymers may be, for example, crosslinked homopolymers or copolymers.

The present invention relates inter alia to polymers containing units derived from bio-based acryloyldimethyltaurate (ACDMT) and similar compounds. The preparation method of ACDMT typically comprises the use of acrylonitrile, isobutene and a mixture of sulfuric acid and fuming sulfuric acid comprising sulfur trioxide. Preferably, at least one of the raw materials, acrylonitrile or isobutene, are of bio-based origin. The bio-based ACDMT is suitable to make polymers comprising a bio-based carbon content stemming from its bio-based ACDMT share.

ACDMT (see Formula [3]) consists of seven carbon atoms. Preferably a minimum of three, preferably four and most preferred all seven carbon atoms of the ACDMT molecule can become renewable, bio-based carbon atoms. In this way, a high proportion of bio-based and/or biodegradable (polymer) products made from the bio-based monomer ACDMT are recyclable and part of the natural carbon cycle. If these kinds of products are incinerated or biodegraded, the quantity of carbon dioxide that is emitted corresponds to the quantity fixed by photosynthesis during biomass growth.

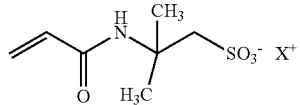

(3)

To date several high performance water soluble or water swellable polymers such as Fluid Loss Additives for the construction and (oil and gas) well construction industry as well as rheology modifiers, comprise ACDMT. Independent from the excellent performance in their applications, such polymers have so-far all been made from petrochemical based, fossil hydrocarbon based ACDMT. The present invention provides new polymers comprising units from bio-based ACDMT or similar compounds (see Formula (1)), thus giving access to new bio-based polymers having the excellent performance benefits that such conventionally synthetic polymers are known for.

The details of the invention and its aspects are provided hereinafter.

First Aspect

In a first aspect, the present invention relates to a polymer comprising:

(a) from 90 mol-% to 99.9 mol-%, preferably from 95 mol-% to 99.5 mol-% of repeating units according to Formula (1) wherein at least 10 wt.-%, preferably at least 20 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

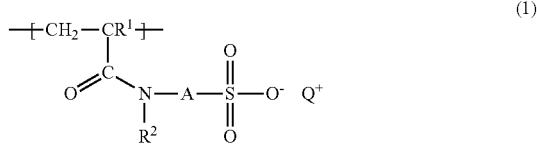

(1)

wherein:

R$^1$ and R$^2$ are independently selected from H, methyl or ethyl; A is a linear or branched C$_1$-C$_{12}$-alkyl group; and Q$^+$ is H$^+$, NH$_4^+$, organic ammonium ions [NHR$^5$R$^6$R$^7$]$^+$ wherein R$^5$, R$^6$, and R$^7$ independently of one another may be hydrogen, a linear or branched alkyl group having 1 to 22 carbon atoms, a linear or branched, singularly or multiply unsaturated alkenyl group having 2 to 22 carbon atoms, a C$_6$-C$_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$, ⅓ $Al^{+++}$, or combinations thereof;

(b) from 0.01 mol-% to 10 mol-%, preferably from 0.01 mol-% to 5 mol-% of crosslinking or branching units, wherein the crosslinking or branching units result from the incorporation of a monomer comprising at least two olefinically unsaturated double bonds.

In at least one embodiment, the polymer comprises from 96 mol-% to 99.7 mol-%, preferably from 97 mol % to 99.5 mol % units (a), and from 0.3 mol-% to 4 mol-%, preferably from 0.5 mol-% to 3 mol-% units (b). In at least one embodiment, the polymer comprises units (a) and (b), such that the sum thereof is at least 99 mol-%, by total weight of the polymer.

In at least one embodiment, the polymer consists of units (a) and (b).

In at least one embodiment, the polymer has a weight average molecular weight of at least 700 g/mol, preferably from 700 g/mol to 10 million g/mol.

In at least one embodiment, the polymer is a derived natural cosmetic ingredient. According to ISO 16128-1:2016 (E) a polymer is a derived natural cosmetic ingredient if it is of greater than 50% natural origin by renewable carbon content. The degree of natural origin can be quantified by renewable carbon content according to analytical procedure ASTM 6866-12, Method B.

Units (a)

In at least one embodiment, the polymer comprises at least one repeating unit (a) according to Formula (1) wherein $R^1$ and $R^2$ are independently selected from H, methyl or ethyl; A is a linear or branched $C_1$-$C_{12}$-alkyl group; and $Q^+$ is $H^+$, $NH_4^+$, $Li^+$, $Na^+$, $K^+$, ½ $Ca^{++}$, ½ $Mg^{++}$, ½ $Zn^{++}$, ⅓ $Al^{+++}$, or combinations thereof, preferably wherein $Q^+$ is $Na^+$ or $NH_4^+$. $NH_4^+$ is preferred because it is more soluble the favored solvent used in the polymer synthesis. $Na^+$ is preferred because of reduced likelihood of unpreferred gases being produced during synthesis and also due to economic advantages.

In at least one embodiment, $Q^+$ is $NH_4^+$. In at least one embodiment, $Q^+$ is selected from the group monoalkylammonium, dialkylammonium, trialkylammonium and/or tetraalkylammonium salts, in which the alkyl substituents of the amines may independently of one another be ($C_1$ to $C_{22}$)-alkyl radicals or ($C_2$ to $C_{10}$)-hydroxyalkyl radicals.

In at least one embodiment, the polymer comprises at least one repeating unit (a) according to Formula (1). In at least one embodiment, the polymer comprises two or more different repeating units (a) according to Formula (1), such as repeating units according to Formula (1) having different $Q^+$ counterions.

In at least one embodiment, the repeating units (a) according to Formula (1) have a degree of neutralisation of between 0 mol-% and 100 mol-%. In at least one embodiment, the repeating units (a) according to Formula (1) have a degree of neutralisation of from 50.0 to 100 mol-%, preferably from 80 mol-% to 100 mol-%, more preferably from 90.0 to 100 mol-%, even more preferably from 95.0 to 100 mol-%. Particular preference being given to a degree of neutralisation of more than 80 mol-%, more preferably more than 90 mol-%, even more preferably more than 95 mol-%. The degree of neutralisation is important in view of the molecular weight of the polymer and the yield of polymer produced.

At least 10 wt.-%, preferably at least 20 wt.-% of the repeating units (a) according to Formula (1) comprise from 28 wt.-% to 100 wt.-% bio-based carbon content, relative to the total mass of carbon in the repeating unit (a) according to Formula (1), measured according to standard ASTM D6866-12, Method B. In at least one embodiment, at least 25 wt.-%, or at least 30 wt.-%, or at least 35 wt.-%, or at least 40 wt.-%, or at least 45 wt.-%, or at least 50 wt.-%, or at least 55 wt.-%, or at least 60 wt.-%, or at least 65 wt.-%, or at least 70 wt.-%, or at least 75 wt.-%, or at least 80 wt.-%, or at least 85 wt.-%, or at least 90 wt.-%, or at least 95 wt.-%, or at least 96 wt.-%, or at least 97 wt.-%, or at least 98 wt.-%, or at least 99 wt.-%, or at least 99.5 wt.-% of the repeating units according to Formula (1) comprise from 28 wt.-% to 100 wt.-% bio-based carbon content, relative to the total mass of carbon in the repeating unit (a) according to Formula (1), measured according to standard ASTM D6866-12, Method B.

In at least one embodiment, the repeating units according to Formula (1) comprise from 28 wt.-% to 100 wt.-% bio-based carbon content, relative to the total mass of carbon in the repeating unit according to Formula (1), measured according to standard ASTM D6866-12, Method B. In at least one embodiment, the repeating unit (a) comprises from 35 wt.-%, preferably from 40 wt.-%, more preferably from 54 wt.-%, even more preferably from 57 wt.-% to 100 wt.-%, most preferably about 100 wt.-%, bio-based carbon content, relative to the total mass of carbon in the repeating unit according to Formula (1), measured according to standard ASTM D6866-12, Method B.

In at least one embodiment, the repeating units according to Formula (1) result from the incorporation of a monomer selected from the group consisting of acryloyldimethyltaurates, acryloyl-1,1-dimethyl-2-methyltaurates, acryloyltaurates, acryloyl-N-methyltaurates, and combinations thereof. Preferably the repeating units (a) according to Formula (1) result from the incorporation of acryloyldimethyltaurate.

In at least one embodiment, the polymer comprises from 95 mol-% to 99.9 mol-%, preferably at least 95.5 mol-%, or at least 96.0 mol-%, or at least 96.5 mol-%, or at least 97 mol-%, or at least 97.5 mol-%, or at least 98 mol-%, or at least 98.5 mol-%, or at least 99 mol-% of repeating units (a) according to Formula (1); preferably wherein at least 30 wt.-%, preferably 50 wt.-%, more preferably 70 wt.-% of the repeating units comprise from 28 wt.-% to 100 wt.-% bio-based carbon content, relative to the total mass of carbon in the repeating unit, measured according to standard ASTM D6866-12, Method B.

In at least one embodiment, the polymer comprises from 95 mol-% to 98 mol-% of repeating units according to Formula (1) wherein at least 30%, preferably 50%, more preferably 70% of the repeating units comprises from 28 wt.-% to 100 wt.-% bio-based carbon content, relative to the total mass of carbon in the repeating unit, measured according to standard ASTM D6866-12, Method B.

Preferably the repeating units according to Formula (1) are incorporated by the polymerization of a compound according Formula (3), wherein X is a proton. More preferably the compound according to Formula (3) is ACDMT.

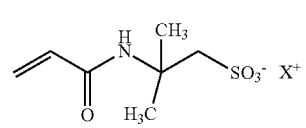

(3)

In at least one embodiment, the ACDMT comprises from 35 wt.-%, preferably from 40 wt.-%, more preferably from 54 wt.-%, even more preferably from 57 wt.-% to 100 wt.-%, most preferably about 100 wt.-%, bio-based carbon content, relative to the total mass of carbon in ACDMT, measured according to standard ASTM D6866-12, Method B.

The bio-based carbon content, relative to the total mass of carbon in repeating units (a) according to Formula (1), is measured according to standard ASTM D6866-12, Method B. More details on the analytical procedure for determination of bio-based carbon content: the provided sample material does not undergo any pre-treatment procedure and is converted to graphite as is using the following procedure:

Depending on the estimated amount of carbon content, typically a few milligrams of sample material is combusted in an elemental analyzer (EA). The resulting gas mixture is cleaned and $CO_2$ is automatically separated by the EA using the purge and trap technology. The remaining $CO_2$ is transferred into a custom-made graphitization system, converted into carbon (graphite) catalytically using $H_2$ and an iron-powder catalyst. The carbon-14 determination of the graphite is performed at the Klaus-Tschira-Archaeometrie-Center using an accelerator mass-spectrometer (AMS) of the type MICADAS (developed at the ETH Zurich, Switzerland).

Units (b)

The polymer comprises crosslinking or branching units (b), wherein the crosslinking or branching units result from the incorporation of a monomer comprising at least two olefinically unsaturated double bonds. The polymer comprises from 0.01 mol-% to 10 mol-%, preferably 0.01 mol-% to 5 mol-%, more preferably from 0.01 mol-% to 3 mol-% of crosslinking or branching units.

In at least one embodiment, the crosslinking or branching units comprise least one oxygen, nitrogen, and sulfur or phosphorus atom. In at least one embodiment, the crosslinking or branching units result from the incorporation of monomers having a molecular weight of less than 500 g/mol. In at least one embodiment, the crosslinking or branching units (b) are bifunctional or trifunctional crosslinking agents.

In at least one embodiment, the polymer comprises two or more different crosslinking or branching units.

In at least one embodiment, the crosslinking or branching units result from the incorporation of a monomer according to Formula (2):

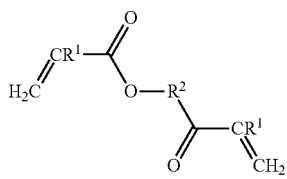

(2)

wherein
$R^1$ is independently selected from H, methyl or ethyl; and
$R^2$ is a linear or branched alkyl group having 1 to 6 carbon atoms, or is a linear or branched, mono- or polyunsaturated alkylene group having 2 to 6 carbon atoms, —$(CH_2$—$CH_2$—$O)_n$—;
n is a real number between 1 and 100.

A monomer according to Formula (2) has the advantage that the polymer can be predicted as more brush-like in structure. However, brush-like polymers show different properties versus linear ones. For example, depending on the different comonomer units the solubility could in- or decreased.

In at least one embodiment, the crosslinking or branching units result from the incorporation of a monomer according to Formula (4)

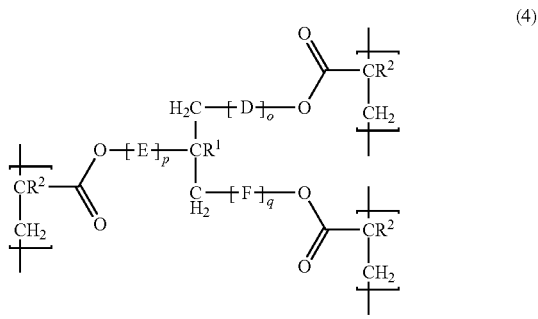

(4)

wherein
$R^1$ is independently selected from H, methyl or ethyl; and
$R^2$ is a linear or branched alkyl group having 1 to 6 carbon atoms, or is a linear or branched, mono- or polyunsaturated alkylene group having 2 to 6 carbon atoms;
D, E, and F are independently methyleneoxy(—$CH_2O$), ethyleneoxy(—$CH_2$—$CH_2$—O—), propyleneoxy(—CH($CH_3$)—$CH_2$—O—), a linear or branched alkylene group having 1 to 6 carbon atoms, a linear or branched, singularly or multiply unsaturated alkenylene group having 2 to 6 carbon atoms, a linear mono-hydroxyalkylene group having 2 to 6 carbon atoms or a linear or branched dihydroxyalkylene group having 3 to 6 carbon atoms; and
o, p, and q each independently are an integer from 1 to 50.

A monomer according to Formula (4) has the advantage that a polymer can be predicted as being highly branched.

In at least one embodiment, the crosslinking or branching units result from the incorporation of a monomer selected from the group consisting of methylenebisacrylamide; methylenebismethacrylamide; esters of unsaturated monocarboxylic and polycarboxylic acids with polyols, preferably di-acrylates and tri-acrylates and -methacrylates (e.g. glycerol propoxylate triacrylate [GPTA]), more preferably butanediol and ethylene glycol diacrylate and poly ethylene glycol diacrylate and -methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives. The choice of crosslinking or branching units is important in view of the flexibility of the crosslinks between the main chains of the polymer which affects the final performance of the polymer.

In at least one embodiment, the crosslinking or branching units (b) result from the incorporation of a crosslinker selected from the group consisting of trimethylolpropane triacrylate (TMPTA) and/or glycerol propoxylate triacrylate (GPTA). Particularly preferred as crosslinkers for the polymers of the invention are glycerol propoxylate triacrylate (GPTA), trimethylolpropane triacrylate (TMPTA), pentaerythritol diacrylate mono stearate (PEAS), hexanediol diacrylate (HDDA), poly ethylene glycol diacrylate (PEG-DA) and hexanediol dimethacrylate (HDDMA). Especially preferred is glycerol propoxylate triacrylate (GPTA) and trimethylolpropane triacrylate (TMPTA).

Units (c)

In at least one embodiment, the polymer at least one repeating neutral structural unit.

In at least one embodiment, the polymer comprises (c) from 0.99 mol-% to 59.99 mol-%, preferably from 1.99 mol-% to 44.99 mol-% of repeating neutral structural units; wherein the repeating neutral units comprises up to 100 wt.-% bio-based carbon content, relative to the total mass of carbon in the repeating unit, measured according to standard ASTM D6866-12, Method B.

In at least one embodiment, the polymer comprises at least one repeating neutral structural unit selected from the group consisting of N-vinylformamide, N-vinylacetamide, N-methyl-N-vinylformamide, N-methyl-N-vinylacetamide, N-vinyl-2-pyrrolidone, N-vinylcaprolactam, vinylacetate, N,N-dimethylacrylamide, N-isopropylacrylamide, acrylamide, methylacrylate, behenylpolyethoxy-(25)-methacrylate, laurylpoly-ethoxy-(7)-methacrylate, cetylpolyethoxy-(10)-methacrylate, stearylpoly-ethoxy-(8)-methacrylate, methoxypoly-ethoxy-(12)-methacrylate, and combinations thereof.

Units (d)

In at least one embodiment, the polymer comprises at least one repeating anionic structural unit (d).

In at least one embodiment, the polymer comprises from 1.98 mol-% to 20 mol-%, preferably from 2.5 mol-% to 18 mol-% of repeating anionic structural units, wherein the repeating anionic structural units result from the incorporation of a monomer comprising at least one carboxylate anion, and wherein the repeating anionic structural units (d) are different from units (a) and wherein the repeating anionic structural units comprises up to 100 wt.-% bio-based carbon content, relative to the total mass of carbon in the repeating unit, measured according to standard ASTM D6866-12, Method B.

In at least one embodiment, the repeating anionic structural unit results from the incorporation of monomers according to formula (A):

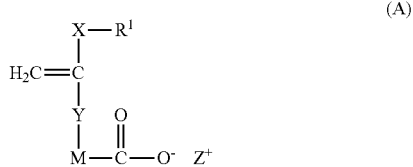

(A)

wherein $R^1$ and $R^3$ are H, methyl or ethyl, or $C(O)O^-Z^+$;

X, Y are selected from a covalent bond, O, $CH_2$, O(O)O, OC(O), $C(O)NR^3$ or $NR^3C(O)$;

M are selected from a covalent bond, —[C(O)O—$CH_2$—$CH_2$]$_n$—, a linear or branched alkylene group with 1 to 6 carbon atoms, a linear or branched, mono- or polyunsaturated alkenylene group with 2 to 6 carbon atoms, a linear mono-hydroxyalkylene group with 2 to 6 carbon atoms or a linear or branched di-hydroxyalkylene group with 3 to 6 carbon atoms;

n is an integer from 1 to 5; and $Z^+$ is $H^+$, $NH_4^+$, an organic ammonium ion $[HNR^5R^6R^7]^+$ wherein $R^5$, $R^6$ and $R^7$ are independently hydrogen, a linear or branched alkyl group with 1 to 22 carbon atoms, a linear or branched, mono- or polyunsaturated alkenyl group with 2 to 22 carbon atoms, a $C_6$ to $C_{22}$ alkylamidopropyl group, a linear mono-hydroxyalkyl group with 2 to 10 carbon atoms or a linear or branched di-hydroxyalkyl group with 3 to 10 carbon atoms, and wherein at least one of $R^5$, $R^6$ and $R^7$ is not hydrogen, or $Z^+$ is $Li^+$, $Na^+$, $K^+$, ½ $Ca^{++}$, ½ $Mg^{++}$, ½ $Zn^{++}$, ⅓ $Al^{+++}$, or combinations thereof. In at least one embodiment, the $Z^+$ is $H^+$, $NH_4^+$, $Li^+$, $Na^+$, $K^+$, ½ $Ca^{++}$, ½ $Mg^{++}$, ½ $Zn^{++}$, or ⅓ $Al^{+++}$, preferably $H^+$, $NH_4^+$, $Li^+$, $Na^+$ or $K^+$.

In at least one embodiment, the polymer comprises at least one repeating anionic structural unit selected from the group consisting of acrylic acid or acrylate methacrylic acid or methacrylate, itaconic acid or itaconate, carboxyethylacrylic acid or carboxyethylacrylate, carboxyethylacrylic acid oligomers or carboxyethylacrylate oligomers, 2-propylacrylic acid or 2-propylacrylate, 2-ethylacrylic acid or 2-ethylacrylate, and their respective alkali or alkaline earth metal salts.

In at least one embodiment, the polymer comprises at least one repeating anionic structural unit selected from the group consisting of acrylic acid or acrylate methacrylic acid or methacrylate, itaconic acid or itaconate, carboxyethylacrylic acid or carboxyethylacrylate, carboxyethylacrylic acid oligomers or carboxyethylacrylate oligomers, and their respective alkali or alkaline earth metal salts. These repeating anionic structural units are preferred because they can easily be synthesised from bio-based sources.

Optional Units (e)

In at least one embodiment, the polymer comprises at least one optional unit. In at least one embodiment, the optional unit results from the incorporation of a monomer selected from the group consisting of unsaturated carboxylic acids and their anhydrides and salts, and also their esters with aliphatic, olefinic, cycloaliphatic, arylaliphatic or aromatic alcohols having a carbon number of from 1 to 22. In at least one embodiment, the optional unit results from the incorporation of at least one monomer selected from the group consisting of functionalised (meth)acrylic acid esters, acrylic or methacrylic acid amides, polyglycol acrylic or methacrylic acid esters, polyglycol acrylic or methacrylic acid amides, dipropyleneglycolacrylic or methacrylic acid esters, dipropylenglycolacrylic or methacrylic acid amides, ethoxylated fatty alcohol acrylates or -methacrylates, propoxylated fatty alcohol acrylates or linear or cyclic N-vinylamides or N-methylvinyl amides.

In at least one embodiment, the optional unit results from the incorporation of monomers according to formula (A):

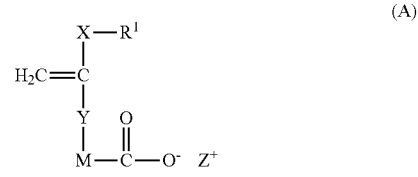

(A)

wherein:

X, Y are selected from a covalent bond, O, $CH_2$, C(O)O, OC(O), $C(O)NR^3$ or $NR^3C(O)$;

$R^1$ and $R^3$ are H, methyl or ethyl, or $C(O)O^-Z^+$;

M is selected from a covalent bond, —[C(O)O—$CH_2$—$CH_2$]$_n$—, a linear or branched alkylene group with 1 to 6 carbon atoms, a linear or branched, mono- or polyunsaturated alkenylene group with 2 to 6 carbon atoms, a linear mono-hydroxyalkylene group with 2 to 6 carbon atoms or a linear or branched di-hydroxyalkylene group with 3 to 6 carbon atoms;

n is an integer from 1-5, and $Z^+$ is $H^+$, $NH_4^+$, an organic ammonium ion $[HNR^5R^6R^7]^+$ wherein $R^5$, $R^6$ and $R^7$ are independently hydrogen, a linear or branched alkyl group with 1 to 22 carbon atoms, a linear or branched, mono- or polyunsaturated alkenyl group with 2 to 22 carbon atoms, a $C_6$ to $C_{22}$ alkylamidopropyl group, a linear mono-hydroxyalkyl group with 2 to 10 carbon atoms or a linear or branched di-hydroxyalkyl group with 3 to 10 carbon atoms, and wherein at least one of $R^5$, $R^6$ and $R^7$ is not hydrogen, or $Z^+$ is $Li^+$, $Na^+$, $K^+$, ½ $Ca^{++}$, ½ $Mg^{++}$, ½ $Zn^{++}$, ⅓ $Al^{+++}$, or combinations thereof. In at least one embodiment, the $Z^+$ is $H^+$, $NH_4^+$, $Li^+$, $Na^+$, $K^+$, ½ $Ca^{++}$, ½ $Mg^{++}$, ½ $Zn^{++}$, or ⅓ $Al^{+++}$, preferably $H^+$, $NH_4^+$, $Li^+$, $Na^+$ or K.

In at least one embodiment, the optional unit results from the incorporation of a monomer according to formula (A) wherein X is a covalent bond or is $CH_2$. In at least one embodiment, the optional unit results from the incorporation of a monomer according to formula (A) wherein Y is a covalent bond, $CH_2$, C(O)O, or C(O)$NR^3$. In at least one embodiment, the optional unit results from the incorporation of a monomer according to formula (A) wherein M is a covalent bond, —[C(O)O—$CH_2$—$CH_2$]n-, a linear or branched alkylene group with 1 to 6 carbon atoms. In at least one embodiment, the optional unit results from the incorporation of a monomer according to formula (A) wherein $R^1$ is H, methyl or ethyl; X is a covalent bond or is $CH_2$; Y is a covalent bond, $CH_2$, C(O)O, or C(O)$NR^3$; $R^3$ is H, methyl or ethyl; M is a covalent bond, —[C(O)O—$CH_2$—$CH_2$]n-, a linear or branched alkylene group with 1 to 6 carbon atoms; $Z^+$ is $H^+$, $NH_4^+$, $Li^+$, $Na^+$, $K^+$, ½ $Ca^{++}$, ½ $Mg^{++}$, ½ $Zn^{++}$, or ⅓ $Al^{+++}$, or combinations thereof.

In at least one embodiment, the optional unit results from the incorporation of a monomer selected from the group consisting of N-vinylformamide, N-vinylacetamide, N methyl-N-vinylformamide, N-methyl-N-vinylacetamide, N-vinyl-2-pyrrolidone (NVP), N vinylcaprolactam, vinylacetate, methylvinylether, ethylvinylether, methylallylether, ethylmethallylether, styrol, acetoxystyrol, methylmethallylether, ethylallylether, tert-butylacrylamide, N,N-diethylacrylamide, N,N-dimethylacrylamide, N,N-dimethylmethacrylamide, N,N-dipropylacrylamide, N-isopropylacrylamide, N-propylacrylamide, acrylamide, methacrylamide, methylacrylate, methymethylacrylate, tert-butylacrylate, tert-butylmethacrylate, n-butylacrylate, n-butylmethacrylate, laurylacrylate, laurylmethacrylate, behenylacrylate, behenylmethacrylate, cetylacrylate, cetylmethacrylate, stearylacrylate, stearylmethacrylate, tridecylacrylate, tridecylmethacrylate, polyethoxy-(5)-methacrylate, polyethoxy-(5)-acrylate, polyethoxy-(10)-methacrylate, polyethoxy-(10)-acrylate, behenylpolyethoxy-(7)-methacrylate, behenylpolyethoxy-(7)-acrylate, behenylpolyethoxy-(8)-methacrylate, behenylpoly-ethoxy-(8)-acrylate, behenylpolyethoxy-(12)-methacrylate, behenylpoly-ethoxy-(12)-acrylate, behenylpolyethoxy-(16)-methacrylate, behenylpolyethoxy-(16)-acrylate, behenylpolyethoxy-(25)-methacrylate, behenylpolyethoxy-(25)-acrylate, laurylpoly-ethoxy-(7)-methacrylate, laurylpolyethoxy-(7)-acrylate, laurylpolyethoxy-(8)-methacrylate, laurylpolyethoxy-(8)-acrylate, laurylpolyethoxy-(12)-methacrylate, laurylpolyethoxy-(12)-acrylate, laurylpolyethoxy-(16)-methacrylate, laurylpolyethoxy-(16)-acrylate, laurylpolyethoxy-(22)-methacrylate, laurylpolyethoxy-(22)-acrylate, laurylpolyethoxy-(23)-methacrylate, laurylpolyethoxy-(23)-acrylate, cetyl polyethoxy-(2)-methacrylate, cetylpolyethoxy-(2)-acrylate, cetyl polyethoxy-(7)-methacrylate, cetyl polyethoxy-(7)-acrylate, cetylpolyethoxy-(10)-methacrylate, cetylpolyethoxy-(10)-acrylate, cetylpolyethoxy-(12)-methacrylate, cetylpolyethoxy-(12)-acrylate cetylpoly-ethoxy-(16)-methacrylate, cetylpolyethoxy-(16)-acrylate cetyl polyethoxy-(20)-methacrylate, cetyl polyethoxy-(20)-acrylate, cetyl polyethoxy-(25)-methacrylate, cetyl polyethoxy-(25)-acrylate, cetyl polyethoxy-(25)-methacrylate, cetyl polyethoxy-(25)-acrylate, stearylpolyethoxy-(7)-methacrylate, stearylpolyethoxy-(7)-acrylate, stearylpoly-ethoxy-(8)-methacrylate, stearylpolyethoxy-(8)-acrylate, stearylpolyethoxy-(12)-methacrylate, stearylpolyethoxy-(12)-acrylate, stearylpoly-ethoxy-(16)-methacrylate, stearylpolyethoxy-(16)-acrylate, stearylpolyethoxy-(22)-methacrylate, stearylpoly-ethoxy-(22)-acrylate, stearylpolyethoxy-(23)-methacrylate, stearylpolyethoxy-(23)-acrylate, stearylpolyethoxy-(25)-methacrylate, stearylpolyethoxy-(25)-acrylate, tridecylpoly-ethoxy-(7)-methacrylate, tridecylpolyethoxy-(7)-acrylate, tridecylpolythoxy-(10)-methacrylate, tridecylpolyethoxy-(10)-acrylate, tridecylpolyethoxy-(12)-methacrylate, tridecylpolyethoxy-(12)-acrylate, tridecylpolyethoxy-(16)-methacrylate, tridecylpolyethoxy-(16)-acrylate, tridecyl polyethoxy-(22)-methacrylate, tridecylpoly-ethoxy-(22)-acrylate, tridecylpolyethoxy-(23)-methacrylate, tridecylpolyethoxy-(23)-acrylate, tridecylpoly-ethoxy-(25)-methacrylate, tridecylpolyethoxy-(25)-acrylate, methoxypolyethoxy-(7)-methacrylate, methoxy-polyethoxy-(7)-acrylate, methoxypoly-ethoxy-(12)-methacrylate, methoxypoly-ethoxy-(12)-acrylate, methoxypolyethoxy-(16)-methacrylate, methoxypolyethoxy-(16)-acrylate, methoxypoly-ethoxy-(25)-methacrylate, methoxy-polyethoxy-(25)-acrylate, acrylic acid, ammonium acrylate, sodium acrylate, potassium acrylate, lithium acrylate, zinc acrylate, calcium acrylate, magnesium acrylate, zirconium acrylate, methacrylic acid, ammonium methacrylate, sodium methacrylate, potassium methacrylate, lithium methacrylate, calcium methacrylate, magnesium methacrylate, zirconium methacrylate, zinc methacrylate, 2-carboxyethylacrylate, ammonium 2-carboxyethylacrylate, sodium 2-carboxyethylacrylate, potassium 2-carboxyethylacrylate, lithium 2 carboxyethylacrylate, zinc 2-carboxyethylacrylate, calcium 2-carboxyethylacrylate, magnesium 2-carboxyethylacrylate, zirconium 2-carboxyethylacrylate, 2-carboxyethylacrylate-oligomere, ammonium 2-carboxyethylacrylate-oligomers, sodium 2-carboxyethylacrylate-oligomers, potassium 2-carboxyethylacrylate-oligomers, lithium 2 carboxyethylacrylate-oligomers, zinc 2-carboxyethylacrylate-oligomers, calcium 2-carboxyethylacrylate-oligomers, magnesium 2-carboxyethylacrylate-oligomers, zirconium 2-carboxyethylacrylate-oligomers, itaconic acid, sodium itaconate, potassium itaconate, lithium itaconate, calcium itaconate, magnesium itaconate, zirconium itaconate, zinc itaconate, 2-ethylacryl acid, ammonium 2-ethylacrylate, sodium 2-ethylacrylate, potassium 2-ethylacrylate, lithium 2-ethylacrylate, calcium 2-ethylacrylate, magnesium 2-ethylacrylate, zirconium 2-ethylacrylate, zinc 2-ethylacrylate, 2-propylacryl acid, ammonium 2-propylacrylate, sodium 2-propylacrylate, potassium 2-propylacrylate, lithium 2-propylacrylate, calcium 2-propylacrylate, magnesium 2-propylacrylate, magnesium 2-propylacrylate, zirconium 2-propylacrylate, zinc 2-propylacrylate, glycerin propoxylate triacrylate (GPTA), trimethylolpropane triacrylate (TMPTA), pentaerythritoldiacrylate monostearate (PEAS), polyethyleneglycol diacrylate, hexanediol diacrylate (HDDA), hexanediol dimethacrylate (HDDMA), and combinations thereof.

In a preferred embodiment, the optional unit results from the incorporation of a monomer selected from the group consisting of glycerine propoxylate triacrylate (GPTA) and trimethylolpropantriacrylate (TMPTA).

In a preferred embodiment, the optional unit results from the incorporation of a monomer selected from the group consisting of N-vinylformamide, N-vinylacetamide, N-methyl-N-vinylacetamide, N-vinyl-2-pyrrolidone (NVP), N,N-diethylacrylamide, acrylamide, methacrylamide, methylacrylate, methylmethylacrylate, tert-Butylacrylate, acrylic acid, methacrylic acid, 2-carboxyethylacrylate, 2-carboxyethylacrylate oligomers, itaconic acid glycerine propoxylate triacrylate (GPTA), trimethylolpropane triacrylate (TMPTA), pentaerythritol diacrylate monostearate (PEAS) and polyethyleneglycol diacrylate.

In at least one embodiment, the optional unit results from the incorporation of a monomer selected from the group consisting of acrylic acid, methacrylic acid, styrenesulfonic acid, maleic acid, fumaric acid, crotonic acid, itaconic acid, and senecic acid. In at least one embodiment, the optional unit results from monomers selected from the group consisting of open-chain N-vinyl amides, preferably N-vinylformamide (VIFA), N-vinylmethylformamide, N-vinylmethylacetamide (VIMA) and N-vinylacetamides; cyclic N-vinyl amides (N-vinyl lactams) with a ring size of 3 to 9, preferably N-vinylpyrrolidones (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide; hydroxyethylmethacryl amide, hydroxypropylmethacrylamide, and mono[2-(methacryloyloxy)ethyl]succinate; N,N-dimethylaminomethacrylate; diethylaminomethylmethacrylate; acrylamideo- and methacrylamideoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; tetrafluoroethylene; and combinations thereof.

Example Embodiments of the First Aspect

A preferred embodiment of the first aspect relates to a polymer consisting of:
(a) from 90 mol-% to 99.9 mol-%, preferably from 95 mol-% to 99.5 mol-% of repeating units according to Formula (1) wherein at least 10 wt.-%, preferably at least 20 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B;

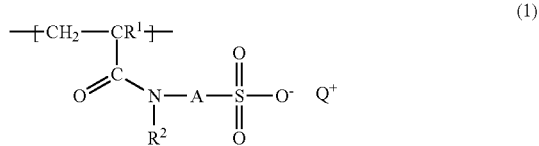

wherein:
$R^1$ and $R^2$ are independently selected from H, methyl or ethyl; A is a linear or branched $C_1$-$C_{12}$-alkyl group; and $Q^+$ is $H^+$, $NH_4^+$, organic ammonium ions $[NHR^5R^6R^7]^+$ wherein $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca'$, ½ $Mg^{++}$, ½ $Zn^{++}$, ⅓ $Al^{+++}$, or combinations thereof;
(b) from 0.01 mol-% to 10 mol-%, preferably from 0.01 mol-% to 5 mol-% of crosslinking or branching units, wherein the crosslinking or branching units result from the incorporation of a monomer comprising at least two olefinically unsaturated double bonds.

A preferred embodiment of the first aspect relates to a polymer comprising: (a) from 90 mol-% to 99.9 mol-%, preferably from 95 mol-% to 99.5 mol-% of a repeating structural unit resulting from the incorporation of ACDMT, wherein the ACDMT comprises from 35 wt.-%, preferably from 40 wt.-%, more preferably from 54 wt.-%, even more preferably from 57 wt.-% to 100 wt.-%, most preferably about 100 wt.-% bio-based carbon content, relative to the total mass of carbon in ACDMT, measured according to standard ASTM D6866-12, Method B.

Second Aspect

A second aspect relates to a process for obtaining a polymer by polymerization of:
(a) at least one monomer according Formula (10) comprising from 28 wt.-% to 100 wt.-% bio-based carbon content, relative to the total mass of carbon in the monomer according to Formula (10), measured according to standard ASTM D6866-12, Method B;
(b) at least one crosslinking or branching monomer;
(c) optionally at least one neutral monomer; and
(d) optionally at least one anionic monomer; wherein the crosslinking or branching monomer has at least two olefinically unsaturated double bonds; and wherein Formula (10) is:

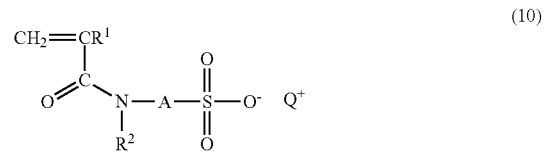

wherein:
$R^1$ and $R^2$ are independently selected from H, methyl or ethyl; A is a linear or branched $C_1$-$C_{12}$-alkyl group; and $Q^+$ is $H^+$, $NH_4^+$, organic ammonium ions $[NHR^5R^6R^7]^+$ wherein $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$, ⅓ $Al^{+++}$, or combinations thereof.

In at least one embodiment, the process for obtaining a polymer by polymerization of:
(a) at least one monomer according to Formula (10) comprising from 28 wt.-% to 100 wt.-% bio-based carbon content, relative to the total mass of carbon in the monomer according to Formula (10), measured according to standard ASTM D6866-12, Method B;
(b) at least one crosslinking or branching monomer;
(c) optionally at least one neutral monomer;
(d) optionally at least one anionic monomer; and
(e) optionally at least one optional monomer; wherein the crosslinking or branching monomer has at least two olefinically unsaturated double bonds.

In at least one embodiment, the polymer is according to the first aspect.

Monomer (a)

In at least one embodiment, at least 25 wt.-%, or at least 30 wt.-%, or at least 35 wt.-%, or at least 40 wt.-%, or at least 45 wt.-%, or at least 50 wt.-%, or at least 55 wt.-%, or at least 60 wt.-%, or at least 65 wt.-%, or at least 70 wt.-%, or at least 75 wt.-%, or at least 80 wt.-%, or at least 85 wt.-%, or at least 90 wt.-%, or at least 95 wt.-%, or at least 96 wt.-%, or at least 97 wt.-%, or at least 98 wt.-%, or at least 99 wt.-%, or at least 99.5 wt.-% of the monomer according Formula (10) comprise from 28 wt.-% to 100 wt.-% bio-based carbon content, relative to the total mass of carbon in the repeating unit according to Formula (1), measured according to standard ASTM D6866-12, Method B. In at least one embodiment, the monomers according Formula (10) comprise from 35 wt.-%, preferably from 40 wt.-%, more preferably from 54 wt.-%, even more preferably from 57 wt.-% to 100 wt.-%, most preferably about 100 wt.-% bio-based carbon content, relative to the total mass of carbon in the repeating unit (a) according to Formula (1), measured according to standard ASTM D6866-12, Method B.

In at least one embodiment, the monomer according Formula (10) is a compound according to Formula (3);

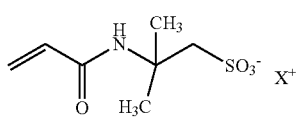

(3)

wherein X is a proton.

In at least one embodiment, the monomer according Formula (10) is ACDMT.

In at least one embodiment, the ACDMT comprises from 35 wt.-%, preferably from 40 wt.-%, more preferably from 54 wt.-%, even more preferably from 57 wt.-% to 100 wt.-%, most preferably about 100 wt.-%, bio-based carbon content, relative to the total mass of carbon in ACDMT, measured according to standard ASTM D6866-12, Method B.

Monomer (b)

In at least one embodiment, the polymer comprises from 0.01 mol-% to 10 mol-%, preferably 0.01 mol-% to 5 mol-%, more preferably from 0.01 mol-% to 3 mol-% of crosslinking or branching units.

In at least one embodiment, the crosslinking or branching units comprise least one oxygen, nitrogen, sulfur or phosphorus atom. In at least one embodiment, the crosslinking or branching units result from monomers having a molecular weight of less than 500 g/mol. In at least one embodiment, the crosslinking or branching units are bifunctional or trifunctional crosslinking agents.

In at least one embodiment, the polymer comprises two or more different crosslinking or branching units.

In at least one embodiment, the crosslinking or branching monomer is according to Formula (2):

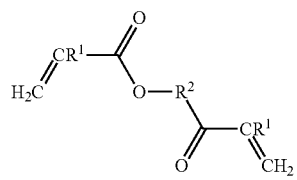

(2)

wherein
R$^1$ is independently selected from H, methyl or ethyl; and
R$^2$ is a linear or branched alkyl group having 1 to 6 carbon atoms, or is a linear or branched, mono- or polyunsaturated alkylene group having 2 to 6 carbon atoms, —(CH$_2$—CH$_2$—O)$_n$—
n is a real number between 1 and 100

A monomer according to Formula (2) has the advantage that the polymer can be predicted as a more brush-like polymer. However brush-like polymers show different properties, as linear ones. For example depending on the different comonomer units the solubility could in- or decreased.

In at least one embodiment, the crosslinking or branching monomer is according to Formula (40)

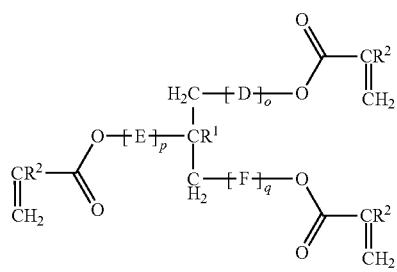

(40)

wherein
R$^1$ is independently selected from H, methyl or ethyl; and
R$^2$ is a linear or branched alkyl group having 1 to 6 carbon atoms, or is a linear or branched, mono- or polyunsaturated alkylene group having 2 to 6 carbon atoms;
D, E, and F are independently methyleneoxy(—CH$_2$O), ethyleneoxy(—CH$_2$—CH$_2$—O—), propyleneoxy(—CH(CH$_3$)—CH$_2$—O—), a linear or branched alkylene group having 1 to 6 carbon atoms, a linear or branched, singularly or multiply unsaturated alkenylene group having 2 to 6 carbon atoms, a linear mono-hydroxyalkylene group having 2 to 6 carbon atoms or a linear or branched dihydroxyalkylene group having 3 to 6 carbon atoms; and
o, p, and q each independently are an integer from 1 to 50.

A monomer according to Formula (40) has the advantage that a polymer can be predicted as being highly branched.

In at least one embodiment, the crosslinking or branching monomer is selected from the group consisting of methylenebisacrylamide; methylenebismethacrylamide; esters of unsaturated monocarboxylic and polycarboxylic acids with polyols, preferably di-acrylates and tri-acrylatees and -methacrylates (e.g. glycerol propoxylate triacrylatee [GPTA]), more preferably butanediol and ethylene glycol diacrylate and poly ethylene glycol diacrylate and -methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives. The choice of crosslinking or branching monomer is important in view of the flexibility of the crosslinks between the main chains of the polymer which affects the final performance of the polymer.

In at least one embodiment, the crosslinking or branching monomer is selected from trimethylolpropane triacrylatee (TMPTA) and/or glycerol propoxylate triacrylate (GPTA).

Particularly preferred as crosslinking or branching monomer for the polymers of the invention are glycerol propoxylate triacrylate (GPTA), trimethylolpropane triacrylate (TMPTA), pentaerythritol diacrylate mono stearate (PEAS), hexanediol diacrylate (HDDA), poly ethylene glycol diacrylate (PEG-DA) and hexanediol dimethacrylate (HDDMA). Especially preferred is glycerol propoxylate triacrylatee (GPTA) and trimethylolpropane triacrylatee (TMPTA).

Monomer (c)

In at least one embodiment, the polymer comprises at least one repeating neutral structural units.

In at least one embodiment, the polymer comprises (c) from 0.99 mol-% to 59.99 mol-%, preferably from 1.99 mol-% to 44.99 mol-% of repeating neutral structural units; wherein the repeating neutral units comprises up to 100 wt.-% bio-based carbon content, relative to the total mass of carbon in the repeating unit, measured according to standard ASTM D6866-12, Method B. In at least one embodiment, at least 25 wt.-%, or at least 30 wt.-%, or at least 35 wt.-%, or at least 40 wt.-%, or at least 45 wt.-%, or at least 50 wt.-%, or at least 55 wt.-%, or at least 60 wt.-%, or at least 65 wt.-%, or at least 70 wt.-%, or at least 75 wt.-%, or at least 80 wt.-%, or at least 85 wt.-%, or at least 90 wt.-%, or at least 95 wt.-%, or at least 96 wt.-%, or at least 97 wt.-%, or at least 98 wt.-%, or at least 99 wt.-%, or at least 99.5 wt.-% of the monomers (c) comprise from 28 wt.-% to 100 wt.-% bio-based carbon content, relative to the total mass of carbon in the repeating unit according to Formula (1), measured according to standard ASTM D6866-12, Method B.

In at least one embodiment, the neutral monomer is selected from the group consisting of N-vinylformamide, N-vinylacetamide, N-methyl-N-vinylformamide, N-methyl-N-vinylacetamide, N-vinyl-2-pyrrolidone, N-vinylcaprolactam, vinylacetate, N,N-dimethylacrylamide, N-isopropylacrylamide, acrylamide, methylacrylate, behenylpolyethoxy-(25)-methacrylate, laurylpoly-ethoxy-(7)-methacrylate, cetylpolyethoxy-(10)-methacrylate, stearyl poly-ethoxy-(8)-methacrylate, methoxypoly-ethoxy-(12)-methacrylate, and combinations thereof.

Monomer (d)

In at least one embodiment, the polymer comprises at least one repeating anionic structural unit.

In at least one embodiment, the polymer comprises from 1.98 mol-% to 20 mol-%, preferably from 2.5 mol-% to 18 mol-% of repeating anionic structural units, wherein the repeating anionic structural units result from the incorporation of a monomer comprising at least one carboxylate anion, and wherein the repeating anionic structural units are different from units (a) and wherein the repeating anionic structural units comprises up to 100 wt.-% bio-based carbon content, relative to the total mass of carbon in the repeating unit, measured according to standard ASTM D6866-12, Method B. In at least one embodiment, at least 25 wt.-%, or at least 30 wt.-%, or at least 35 wt.-%, or at least 40 wt.-%, or at least 45 wt.-%, or at least 50 wt.-%, or at least 55 wt.-%, or at least 60 wt.-%, or at least 65 wt.-%, or at least 70 wt.-%, or at least 75 wt.-%, or at least 80 wt.-%, or at least 85 wt.-%, or at least 90 wt.-%, or at least 95 wt.-%, or at least 96 wt.-%, or at least 97 wt.-%, or at least 98 wt.-%, or at least 99 wt.-%, or at least 99.5 wt.-% of the monomers (d) comprise from 28 wt.-% to 100 wt.-% bio-based carbon content, relative to the total mass of carbon in the repeating unit according to Formula (1), measured according to standard ASTM D6866-12, Method B.

In at least one embodiment, the anionic monomer (d) is according to formula (A):

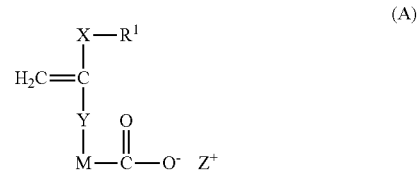

wherein
$R^1$ and $R^3$ are H, methyl or ethyl, or $C(O)O^-Z^+$;
X, Y are selected from a covalent bond, O, $CH_2$, C(O)O, OC(O), $C(O)NR^3$ or $NR^3C(O)$;
M are selected from a covalent bond, $—[C(O)O—CH_2—CH_2]_n—$, a linear or branched alkylene group with 1 to 6 carbon atoms, a linear or branched, mono- or polyunsaturated alkenylene group with 2 to 6 carbon atoms, a linear mono-hydroxyalkylene group with 2 to 6 carbon atoms or a linear or branched di-hydroxyalkylene group with 3 to 6 carbon atoms;
n is an integer from 1-5 and
$Z^+$ is $H^+$, $NH_4^+$, an organic ammonium ion $[HNR^5R^6R^7]^+$ wherein $R^5$, $R^6$ and $R^7$ are independently hydrogen, a linear or branched alkyl group with 1 to 22 carbon atoms, a linear or branched, mono- or polyunsaturated alkenyl group with 2 to 22 carbon atoms, a $C_6$ to $C_{22}$ alkylamidopropyl group, a linear mono-hydroxyalkyl group with 2 to 10 carbon atoms or a linear or branched di-hydroxyalkyl group with 3 to 10 carbon atoms, and wherein at least one of $R^5$, $R^6$ and $R^7$ is not hydrogen, or $Z^+$ is $Li^+$, $Na^+$, $K^+$, ½ $Ca^{++}$, ½ $Mg^{++}$, ½ $Zn^{++}$, ⅓ $Al^{+++}$, or combinations thereof. In at least one embodiment, the $Z^+$ is $H^+$, $NH_4^+$, $Li^+$, $Na^+$, $K^+$, ½ $Ca^{++}$, ½ $Mg^{++}$, ½ $Zn^{++}$, or ⅓ $Al^{+++}$, preferably $H^+$, $NH_4^+$, $Li^+$, $Na^+$ or $K^+$.

In at least one embodiment, the anionic monomer is selected from the group consisting of acrylic acid or acrylate methacrylic acid or methacrylate, itaconic acid or itaconate, carboxyethylacrylic acid or carboxyethylacrylate, carboxyethylacrylic acid oligomers or carboxyethylacrylate oligomers, 2-propylacrylic acid or 2-propylacrylate, 2-ethylacrylic acid or 2-ethylacrylate, and their respective alkali or alkaline earth metal salts.

In at least one embodiment, the anionic monomer is selected from the group consisting of acrylic acid or acrylate methacrylic acid or methacrylate, itaconic acid or itaconate, carboxyethylacrylic acid or carboxyethylacrylate, carboxyethylacrylic acid oligomers or carboxyethylacrylate oligomers, and their respective alkali or alkaline earth metal salts. These anionic monomers are preferred because they can easily synthesised from bio-based sources.

Optional Monomer (e)

In at least one embodiment, the polymer comprises at least one optional unit. In at least one embodiment, the optional monomer is selected from the group consisting of unsaturated carboxylic acids and their anhydrides and salts, and also their esters with aliphatic, olefinic, cycloaliphatic, arylaliphatic or aromatic alcohols having a carbon number of from 1 to 22. In at least one embodiment, the optional monomer is selected from the group consisting of functionalised (meth)acrylic acid esters, acrylic or methacrylic acid amides, polyglycol acrylic or methacrylic acid esters, polyglycol acrylic or methacrylic acid amides, dipropyleneglycolacrylic or methacrylic acid esters, dipropylenglycolacrylic or methacrylic acid amides, ethoxylated fatty alcohol acrylates or -methacrylates, propoxylated fatty alcohol acrylates or linear or cyclic N-vinylamides or N-methylvinyl amides.

In at least one embodiment, the optional monomer is according to formula (A):

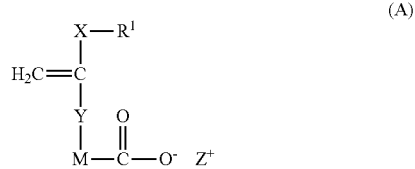

wherein:
X, Y are selected from a covalent bond, O, $CH_2$, C(O)O, OC(O), C(O)$NR^3$ or $NR^3$C(O);
$R^1$ and $R^3$ are H, methyl or ethyl, or C(O)$O^-Z^+$;
M is selected from a covalent bond, —[C(O)O—$CH_2$—$CH_2$]$_n$—, a linear or branched alkylene group with 1 to 6 carbon atoms, a linear or branched, mono- or polyunsaturated alkenylene group with 2 to 6 carbon atoms, a linear mono-hydroxyalkylene group with 2 to 6 carbon atoms or a linear or branched di-hydroxyalkylene group with 3 to 6 carbon atoms;
n is an integer from 1-5, and
$Z^+$ is $H^+$, $NH_4^+$, an organic ammonium ion [$HNR^5R^6R^7$]$^+$ wherein $R^5$, $R^6$ and $R^7$ are independently hydrogen, a linear or branched alkyl group with 1 to 22 carbon atoms, a linear or branched, mono- or polyunsaturated alkenyl group with 2 to 22 carbon atoms, a $C_6$ to $C_{22}$ alkylamidopropyl group, a linear mono-hydroxyalkyl group with 2 to 10 carbon atoms or a linear or branched di-hydroxyalkyl group with 3 to 10 carbon atoms, and wherein at least one of $R^5$, $R^6$ and $R^7$ is not hydrogen, or $Z^+$ is $Li^+$, $Na^+$, $K^+$, ½ $Ca^{++}$, ½ $Mg^{++}$, ½ $Zn^{++}$, ⅓ $Al^{+++}$, or combinations thereof. In at least one embodiment, the $Z^+$ is $H^+$, $NH_4^+$, $Li^+$, $Na^+$, $K^+$, ½ $Ca^{++}$, ½ $Mg^{++}$, ½ $Zn^{++}$, or ⅓ $Al^{+++}$, preferably $H^+$, $NH_4^+$, $Li^+$, $Na^+$ or $K^+$.

In at least one embodiment, the optional monomer is according to formula (A) wherein X is a covalent bond or is $CH_2$. In at least one embodiment, the optional monomer is according to formula (A) wherein Y is a covalent bond, $CH_2$, C(O)O, or C(O)$NR^3$. In at least one embodiment, the optional monomer is according to formula (A) wherein M is a covalent bond, —[C(O)O—$CH_2$—$CH_2$]n-, a linear or branched alkylene group with 1 to 6 carbon atoms. In at least one embodiment, the optional monomer is according to formula (A) wherein $R^1$ is H, methyl or ethyl; X is a covalent bond or is $CH_2$; Y is a covalent bond, $CH_2$, C(O)O, or C(O)$NR^3$; $R^3$ is H, methyl or ethyl; M is a covalent bond, —[C(O)O—$CH_2$—$CH_2$]n-, a linear or branched alkylene group with 1 to 6 carbon atoms; $Z^+$ is $H^+$, $NH_4^+$, $Li^+$, $Na^+$, $K^+$, ½ Ca', ½ $Mg^{++}$, ½ $Zn^{++}$, or ⅓ $Al^{+++}$, or combinations thereof.

In at least one embodiment, the optional monomer (e) is selected from the group consisting of N-vinylformamide, N-vinylacetamide, N methyl-N-vinylformamide, N-methyl-N-vinylacetamide, N-vinyl-2-pyrrolidone (NVP), N vinyl-caprolactam, vinylacetate, methylvinylether, ethylvinylether, methylallylether, ethylmethallylether, styrol, acetoxystyrol, methylmethallylether, ethylallylether, tert-butylacrylamide, N,N-diethylacrylamide, N,N-dimethylacrylamide, N,N-dimethylmethacrylamide, N,N-dipropylacrylamide, N-isopropylacrylamide, N-propylacrylamide, acrylamide, methacrylamide, methylacrylate, methymethylacrylate, tert-butylacrylate, tert.-butylmethacrylate, n-butylacrylate, n-butylmethacrylate, laurylacrylate, laurylmethacrylate, behenylacrylate, behenylmethacrylate, cetylacrylate, cetylmethacrylate, stearylacrylate, stearylmethacrylate, tridecylacrylate, tridecylmethacrylate, polyethoxy-(5)-methacrylate, polyethoxy-(5)-acrylate, polyethoxy-(10)-methacrylate, polyethoxy-(10)-acrylate, behenylpolyethoxy-(7)-methacrylate, behenylpolyethoxy-(7)-acrylate, behenylpolyethoxy-(8)-methacrylate, behenylpoly-ethoxy-(8)-acrylate, behenylpolyethoxy-(12)-methacrylate, behenylpoly-ethoxy-(12)-acrylate, behenylpolyethoxy-(16)-methacrylate, behenylpolyethoxy-(16)-acrylate, behenylpolyethoxy-(25)-methacrylate, behenylpolyethoxy-(25)-acrylate, laurylpoly-ethoxy-(7)-methacrylate, laurylpolyethoxy-(7)-acrylate, laurylpolyethoxy-(8)-methacrylate, laurylpolyethoxy-(8)-acrylate, laurylpolyethoxy-(12)-methacrylate, laurylpolyethoxy-(12)-acrylate, laurylpolyethoxy-(16)-methacrylate, laurylpoly-ethoxy-(16)-acrylate, laurylpolyethoxy-(22)-methacrylate, laurylpolyethoxy-(22)-acrylate, laurylpolyethoxy-(23)-methacrylate, laurylpolyethoxy-(23)-acrylate, cetyl polyethoxy-(2)-methacrylate, cetylpolyethoxy-(2)-acrylate, cetyl polyethoxy-(7)-methacrylate, cetyl polyethoxy-(7)-acrylate, cetylpolyethoxy-(10)-methacrylate, cetylpolyethoxy-(10)-acrylate, cetylpolyethoxy-(12)-methacrylate, cetylpoly-ethoxy-(12)-acrylate cetylpoly-ethoxy-(16)-methacrylate, cetylpolyethoxy-(16)-acrylate cetyl polyethoxy-(20)-methacrylate, cetyl polyethoxy-(20)-acrylate, cetyl polyethoxy-(25)-methacrylate, cetyl polyethoxy-(25)-acrylate, cetyl polyethoxy-(25)-methacrylate, cetyl polyethoxy-(25)-acrylate, stearylpolyethoxy-(7)-methacrylate, stearylpolyethoxy-(7)-acrylate, stearylpoly-ethoxy-(8)-methacrylate, stearylpolyethoxy-(8)-acrylate, stearylpolyethoxy-(12)-methacrylate, stearylpolyethoxy-(12)-acrylate, stearylpoly-ethoxy-(16)-methacrylate, stearylpolyethoxy-(16)-acrylate, stearylpolyethoxy-(22)-methacrylate, stearylpoly-ethoxy-(22)-acrylate, stearylpolyethoxy-(23)-methacrylate, stearylpolyethoxy-(23)-acrylate, stearylpolyethoxy-(25)-methacrylate, stearylpolyethoxy-(25)-acrylate, tridecylpoly-ethoxy-(7)-methacrylate, tridecylpolyethoxy-(7)-acrylate, tridecylpolythoxy-(10)-methacrylate, tridecylpolyethoxy-(10)-acrylate, tridecylpolyethoxy-(12)-methacrylate, tridecylpolyethoxy-(12)-acrylate, tridecylpolyethoxy-(16)-methacrylate, tridecylpolyethoxy-(16)-acrylate, tridecylpolyethoxy-(22)-methacrylate, tridecylpoly-ethoxy-(22)-acrylate, tridecylpolyethoxy-(23)-methacrylate, tridecylpolyethoxy-(23)-acrylate, tridecylpoly-ethoxy-(25)-methacrylate, tridecylpolyethoxy-(25)-acrylate, methoxypolyethoxy-(7)-methacrylate, methoxy-polyethoxy-(7)-acrylate, methoxypoly-ethoxy-(12)-methacrylate, methoxypolyethoxy-(12)-acrylate, methoxypoly-ethoxy-(16)-methacrylate, methoxypolyethoxy-(16)-acrylate, methoxypolyethoxy-(25)-methacrylate, methoxypolyethoxy-(25)-acrylate, acrylic acid, ammonium acrylate, sodium acrylate, potassium acrylate, lithium acrylate, zinc acrylate, calcium acrylate, magnesium acrylate, zirconium acrylate, methacrylic acid, ammonium methacrylate, sodium methacrylate, potassium methacrylate, lithium methacrylate, calcium methacrylate, magnesium methacrylate, zirconium methacrylate, zinc methacrylate, 2-carboxyethylacrylate, ammonium 2-carboxyethylacrylate, sodium 2-carboxyethylacrylate, potassium 2-carboxyethylacrylate, lithium 2 carboxyethylacrylate, zinc 2-carboxyethylacrylate, calcium 2-carboxyethylacrylate, magnesium 2-carboxyethylacrylate, zirconium 2-carboxyethylacrylate, 2-carboxyethylacrylate-oligomere, ammonium 2-carboxyethylacrylate-oligomers, sodium 2-carboxyethylacrylate-oligomers, potassium 2-carboxyethylacrylate-oligomers, lithium 2 carboxyethylacrylate-oligomers, zinc 2-carboxyethylacrylate-oligomers, calcium 2-carboxyethylacrylate-oligomers, magnesium 2-carboxyethylacrylate-oligomers, zirconium 2-carboxyethylacrylate-oligomers, itaconic acid, sodium itaconate, potassium itaconate, lithium itaconate, calcium itaconate, magnesium itaconate, zirconium itaconate, zinc itaconate, 2-ethylacryl acid, ammonium 2-ethylacrylate, sodium 2-ethylacrylate, potassium 2-ethylacrylate, lithium 2-ethylacrylate, calcium 2-ethylacrylate, magnesium 2-ethylacrylate, zirconium 2-ethylacrylate, zinc 2-ethylacrylate, 2-propylacryl acid, ammonium 2-propylacrylate, sodium 2-propylacrylate, potassium 2-propylacrylate, lithium 2-propylacrylate, calcium 2-propylacrylate, magnesium 2-propylacrylate, magnesium 2-propylacrylate, zirconium 2-propylacrylate, zinc 2-propylacrylate, glycerin propoxylate triacrylate (GPTA), trimethylolpropane triacrylate (TMPTA), pentaerythritoldiacrylate monostearate (PEAS), polyethyleneglycol diacrylate, hexanediol diacrylate (HDDA), hexanediol dimethacrylate (HDDMA), and combinations thereof.

In a preferred embodiment, the optional monomer (e) is selected from the group consisting of glycerine propoxylate triacrylate (GPTA) and trimethylolpropantriacrylate (TMPTA).

In a preferred embodiment, the optional monomer (e) is selected from the group consisting of N-vinylformamide, N-vinylacetamide, N-methyl-N-vinylacetamide, N-vinyl-2-pyrrolidone (NVP), N,N-diethylacrylamide, acrylamide, methacrylamide, methylacrylate, methylmethylacrylate, tert-Butylacrylate, acrylic acid, methacrylic acid, 2-carboxyethylacrylate, 2-carboxyethylacrylate oligomers, itaconic acid glycerine propoxylate triacrylate (GPTA), trimethylolpropane triacrylate (TMPTA), pentaerythritol diacrylate monostearate (PEAS) and polyethyleneglycol diacrylate.

In at least one embodiment, the optional monomer (e) is selected from the group consisting of acrylic acid, methacrylic acid, styrenesulfonic acid, maleic acid, fumaric acid, crotonic acid, itaconic acid, and senecic acid. In at least one embodiment, the optional monomer is selected from the group consisting of open-chain N-vinyl amides, preferably N-vinylformamide (VIFA), N-vinylmethylformamide, N-vinylmethylacetamide (VIMA) and N-vinylacetamides;

cyclic N-vinyl amides (N-vinyl lactams) with a ring size of 3 to 9, preferably N-vinylpyrrolidones (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide; hydroxyethylmethacrylamide, hydroxypropylmethacrylamide, and mono[2-(methacryloyloxy)ethyl]succinate; N,N-dimethylaminomethacrylate; diethylaminomethylmethacrylate; acrylamideo- and methacrylamideoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; tetrafluoroethylene; and combinations thereof.

Polymerisation

In at least one embodiment, the above monomers are dissolved or dispersed in a polar solvent. The polymerisation is preferably initiated by the addition of a radical building compound.

In at least one embodiment, the monomer according Formula (10) is neutralised with a base prior to polymerisation.

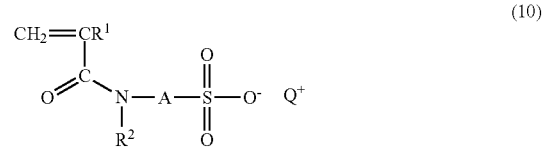

(10)

In at least one embodiment, the monomer according formula (10) is neutralized following polymerization using a base. In at least one embodiment, in the monomer according to Formula (10), $R^1$ and $R^2$ are H; A is —C(CH$_3$)$_2$—H$_2$C—; and $Q^+$ is a cation.

In at least one embodiment, in Formula (10) $Q^+$ is $H^+$, $NH_4^+$, morpholine, an organic ammonium ion $[NHR^5R^6R^7]^+$ wherein $R^5$, $R^6$, and $R^7$ independently of one another is hydrogen, a linear or branched alkyl group having 1 to 22 carbon atoms, a linear or branched, mono- or poly-unsaturated alkenyl group having 2 to 22 carbon atoms, a $C_6$-$C_{22}$ alkylamidopropyl group, a linear mono-hydroxyalkyl group having 2 to 10 carbon atoms or a linear or branched dihydroxyalkyl group having 3 to 15 carbon atoms, and wherein at least one of the radicals $R^5$, $R^6$, and $R^7$ is not hydrogen, or $X^+$ is $Li^+$, $Na^+$, $K^+$, ½ $Ca^{++}$, ½ $Mg^{++}$, ½ $Zn^{++}$, ⅓ $Al^{+++}$, or combinations thereof. Preferably $Q^+$ is $H^+$, $NH_4^+$ or Nat Most preferably, $Q^+$ is $Na^+$ and $NH_4^+$. In at least one embodiment, $Q^+$ is $NH_4^+$. In at least one embodiment, $Q^+$ is selected from the group monoalkylammonium, dialkylammonium, trialkylammonium and/or tetraalkylammonium salts, in which the alkyl substituents of the amines may independently of one another be ($C_1$ to $C_{22}$)-alkyl radicals or ($C_2$ to $C_{10}$)-hydroxyalkyl radicals.

In at least one embodiment, the monomer according to Formula (10) is selected from the group consisting of acryloyldimethyltaurates, acryloyl-1,1-dimethyl-2-methyltaurates, acryloyltaurates, acryloyl-N-methyltaurates, and combinations thereof. Preferably the monomer according to Formula (10) is acryloyldimethyltaurate.

In at least one embodiment, the monomer according to Formula (10) has a degree of neutralisation of between 0 mol-% and 100 mol-%. In at least one embodiment, the monomer according to Formula (10) has a degree of neutralisation of from 50.0 to 100 mol-%, preferably from 80 mol-% to 100 mol-%, more preferably from 90.0 to 100 mol-%, even more preferably from 95.0 to 100 mol-%. Particular preference being given to a degree of neutralisation of more than 80 mol-%, more preferably more than 90 mol-%, even more preferably more than 95 mol-%.

In at least one embodiment, the monomer according to Formula (10) can be neutralized by using gaseous ammonia, ammonia hydroxide solution, morpholine, monoalkylammine, dialkylammine, trialkylammine, tetraalkylammonium salts, sodium hydrogen carbonate, sodium carbonate, sodium hydroxide, potassium hydrogen carbonate, potassium carbonate, potassium hydroxide, lithium hydrogen carbonate, lithium carbonate, lithium hydroxide, preferably gaseous ammonia, morpholine, and sodium hydrogen carbonate.

In at least one embodiment, the synthesis of the polymer is carried out by radical precipitation polymerization in a polar solvent or a polar solvent mixture. Preferably the polar solvent or a polar solvent mixture has a boiling point between 60° C. and 110° C., preferably between 60° C. and 95° C. and more preferably between 60° C. and 95° C.

In at least one embodiment, the radical precipitation polymerization is carried out in a polar solvent mixture comprise:
I) water and
II) a further compound.

In at least one embodiment the compound II) is polar and organic.

In at least one embodiment the compound II) is one or more polar alcohols and one or more ketones.

In a preferred embodiment, the compound II) is selected from the group consisting methanol, ethanol, 1-propanol, 2-propanol, 2-methyl-2-propanol, 1-butanol, 2-butanol, dimethyl ketone, diethyl ketone, pentan-2-one, butanone, tetrahydro pyrane, tetrahydro furane, 2-methyl-tetrahydro furane, 1,3-dioxane, 1,4-dioxane, preferably 2-propanol, 2-methyl-2-propanol, dimethyl ketone, tetrahydro furane, 2-methyl-tetrahydro furane, more preferably 2-methyl-2-propanol and dimethyl ketone.

In a preferred embodiment, the solvent mixture contains from 0.5 up to 10 wt.-%, preferably from 1 up to 8 wt.-% and more preferably from 2 up to 5 wt.-% water.

In a preferred embodiment, the solvent mixture contains from 1 up to 99.5 wt.-%, preferably from 5 up to 95 wt.-% and more preferably from 10 up to 90 wt.-% 2-methyl-2-propanol.

In a preferred embodiment, the polar solvent mixture comprises from 0.5 up to 10 wt.-% water, from 1 up to 98.5 wt.-% 2-methyl-2-propanol and from 1 up to 98.5 wt.-% dimethyl ketone, preferably from 0.5 up to 7.5 wt.-% water, from 5 up to 94.5 wt.-% 2-methyl-2-propanol and from 5 up to 94.5 wt.-% dimethyl ketone.

In a preferred embodiment, the polymerization of the monomers (a) to (b), optionally (a) to (c), optionally (a) to (d), optionally (a) to (e), is carried out in a solvent mixture comprising water, 2-methyl-2-propanol and dimethyl ketone. Preferably the water content of the solvent mixture should not be higher as 10 wt.-%, otherwise the synthesized polymer build lumps during the polymerization.

In a preferred embodiment, the polymerization reaction is initiated by a radical building compound. In at least one embodiment, the radical building compound is selected from the group of azo-initiators (e.g. azo-bis-iso butyronitrile, 2,2'-azobis(4-methoxy-2.4-dimethyl valeronitrile), 2,2'-azobis(2.4-dimethyl valeronitrile), dimethyl 2,2'-azobis(2-methylpropionate), 2,2'-azobis(2-methylbutyronitrile), 1,1'-azobis(cyclohexane-1-carbonitrile) or 2,2'-azobis[N-(2-propenyl)-2-methyl-propionamide]), peroxides (e.g. dilauryl peroxide, tert.-butylhydro peroxide, di-tert.-butyl peroxide, tri phenyl methyl hydroperoxid, benzoylperoxid) or persulfates. In at least one embodiment, the initiation of the polymerization starts in a temperature interval between 30° C. up to 80° C., preferably between 40° C. up to 70° C. during 30 minutes to serial hours.

In at least one embodiment, the polymer has a weight average molecular weight of at least 700 g/mol, preferably from 700 g/mol to 10 million g/mol.

Third Aspect

A third aspect relates to the use of the polymer according to the first aspect as a thickening agent and/or rheology modifier and/or a viscosity modifier. For example, the thickening agent and/or rheology modifier can be used as an additive in the oil and mining industry e.g. to increase the efficiency of processes for isolating crude oil.

A thickening agent or thickener is a substance which can increase the viscosity of a liquid without substantially changing its other properties. Edible thickeners are commonly used to thicken sauces, soups, and puddings without altering their taste; thickeners are also used in paints, inks, explosives, and cosmetics.

Thickeners may also improve the suspension of other ingredients or emulsions which increases the stability of the product. Thickening agents are often regulated as food additives and as cosmetics and personal hygiene product ingredients. Some thickening agents are gelling agents (gellants), forming a gel, dissolving in the liquid phase as a colloid mixture that forms a weakly cohesive internal structure. Others act as mechanical thixotropic additives with discrete particles adhering or interlocking to resist strain.

Thickening agents can also be used when medical condition such as dysphagia cause individuals difficulty when swallowing. Thickened liquids play a vital role in reducing risk of aspiration for dysphagia patients.

Fourth Aspect

A fourth aspect relates to a composition comprising the polymer of the first aspect. In at least one embodiment, the composition comprises at least 0.5 wt.-% of said polymer. In an alternative composition, the composition comprises at least 0.01 wt.-%, or at least 0.05 wt.-%, or at least 0.1 wt.-%, or at least 0.5 wt.-%, or at least 1 wt.-%, or at least 1.5 wt.-%, or at least 2 wt.-%, or at least 2.5 wt.-%, or at least 3 wt.-%, or at least 4 wt.-%, or at least 5 wt.-%, or at least 7.5 wt.-%, or at least 10 wt.-%, or at least 12 wt.-%, or at least 15 wt.-%, or at least 20 wt.-%, or at least 25 wt.-%, or at least 30 wt.-%, or at least 35 wt.-%, or at least 40 wt.-%, or at least 45 wt.-%, or up to 50 wt.-% polymer of the first aspect.

In at least one embodiment, the composition comprises:
(I) the polymer according to the first aspect; and (II) a further component.

In at least one embodiment, the further component is a carrier, solvent or diluent. In at least one embodiment, the composition comprises a solvent, wherein the solvent comprises water and/or alcohol. Solvent is useful for providing the compounds used in present invention in liquid form. In at least one embodiment, the solvent is cosmetically acceptable. In at least one embodiment, the composition comprises at least 10 wt.-% water. Water is useful for economic reasons but also because it is cosmetically acceptable. Optionally the composition comprises water-miscible or water-soluble solvents such as lower alkyl alcohols. In at least one embodiment, the composition comprises $C_1$-$C_5$ alkyl monohydric alcohols, preferably $C_2$-$C_3$ alkyl alcohols. The alcohols which may be present are in particular lower monohydric or polyhydric alcohols having 1 to 4 carbon atoms customarily used for cosmetic purposes, such as preferably ethanol and isopropanol. Optionally, the composition comprises a water-soluble polyhydric alcohol. In at least one embodiment, the water-soluble polyhydric alcohols are polyhydric alcohols having two or more hydroxyl groups in the molecule. In at least one embodiment, the water-soluble polyhydric alcohol is selected from the group consisting of: dihydric alcohols such as ethylene glycol, propylene glycol, trimethylene glycol, 1,2-butylene glycol, 1,3-butylene glycol, 1,4-butylene glycol, tetramethylene glycol, 2,3-butylene glycol, pentamethylene glycol, 2-butene-1,4-diol, hexylene glycol, octylene glycol; trihydric alcohols such as glycerine, trimethylol propane, 1,2,6-hexanetriol and the like; tetrahydric alcohols such as penthaerythritol; pentahydric alcohols such as xylytol, etc.; hexahydric alcohols such as sorbitol, mannitol; polyhydric alcohol polymers such as diethylene glycol, dipropylene glycol, polyethylene glycol, polypropylene glycol, tetraethylene glycol, diglycerine, polyethylene glycol, triglycerine, tetraglycerine, polyglycerine; dihydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether; dihydric alcohol alkyl ethers such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate; glycerine monoalkyl ethers such as xyl alcohol, selachyl alcohol, butyl alcohol; sugar alcohols such as sorbitol, maltitol, maltotriose, mannitol, sucrose, erythritol, glucose, fructose, starch sugar, maltose, xylytose, starch sugar reduced alcohol, glysolid, tetrahydrofurfuryl alcohol, POE tetrahydrofurfuryl alcohol, POP butyl ether, POP POE butyl ether, tripolyoxypropylene glycerine ether, POP glycerine ether, POP glycerine ether phosphoric acid, POP POE pentanerythritol ether, and mixtures thereof. In a preferred embodiment, the composition comprises a solvent selected from the group consisting of water, glycols, ethanol, and combinations thereof. In a preferred embodiment, the composition comprises an aqueous, alcoholic or aqueous-alcoholic solvent, and wherein the aqueous, alcoholic or aqueous-alcoholic solvent comprises water, ethanol, propanol, isopropanol, 1,2-propylene glycol, 1,3-propylene glycol, isobutanol, butanol, butyl glycol, butyl diglycol, glycerol, or a mixture thereof; preferably wherein the aqueous, alcoholic or aqueous-alcoholic solvent comprises water, ethanol, propanol, isopropanol, 1,2-propylene glycol, 1,3-propylene glycol, glycerol, or mixtures thereof; more preferably wherein the aqueous, alcoholic or aqueous-alcoholic solvent comprises water, isopropanol, 1,2-propylene glycol, 1,3-propylene glycol, or mixtures thereof; even more preferably wherein the aqueous, alcoholic or aqueous-alcoholic solvent consists of water or consists of a mixture of water and an alcohol wherein the alcohol is selected from the group consisting of isopropanol, 1,2-propylene glycol and 1,3-propylene glycol. Natural solvents can also be used. In at least one embodiment, the composition comprises a solvent selected from the group consisting of plant oil, honey, plant-derived sugar compositions, and mixtures thereof. In at least one embodiment, the composition comprises from 0.5 wt.-% to 90 wt.-%, preferably from 1.0 wt.-% to 80 wt.-%, even more preferably from 5.0 wt.-% to 70 wt.-% of at least one carrier, solvent and/or diluent.

In at least one embodiment, the composition comprising a polymer according to the first aspect relates to coating and/or adhesive composition. The sulfonic acid group of the polymers according to the first aspect gives an ionic character over a wide range of pH. Anionic charges from these polymers fixed on polymer particles enhance the chemical and shear stabilities of polymer emulsion and also reduce the amount of surfactants leaching out of paint film. It improves the thermal and mechanical properties of adhesives, and increases the adhesive strength of pressure-sensitive adhesive formulations In at least one embodiment, the composition comprising a polymer according to the first aspect relates to a detergent composition. The polymers according to the first aspect enhances the washing performance of surfactants by binding multivalent cations and reducing dirt attachment.

In at least one embodiment, the composition comprising a polymer according to the first aspect relates to personal care composition. The strong polar and hydrophilic properties of the polymers according to the first aspect are exploited as a very efficient lubricant in skin care compositions. The polymers according to the first aspect can be used in bath & shower formulations and in hair care composition.

In at least one embodiment, the composition comprising a polymer according to the first aspect relates to a home care composition. The polymers according to the first aspect can show good performance in dish washing compositions, in fabric care and can be used in surface cleaning compositions.

In at least one embodiment, the composition comprising a polymer according to the first aspect relates to a medical hydrogel. The polymers according to the first aspect demonstrate a high water-absorbing and swelling capacity. Hydrogel with polymers according to the first aspect showed uniform conductivity, low electrical impedance, cohesive strength, appropriate skin adhesion, and biocompatible and capable of repeated use and have been used to electrocardiograph (ECG) electrodes, defibrillation electrode, electrosurgical grounding pads, and iontophoretic drug delivery electrodes. Polymers according to the first aspect can be used as the absorbing hydrogel and the tackifier component of wound dressings.

In at least one embodiment, the composition comprising a polymer according to the first aspect relates to a life sciences composition. The polymers according to the first aspect can be used in pharmaceuticals and in pharmaceutical formulations, in medical manufacturing and in medical devices.

In at least one embodiment, the composition comprising a polymer according to the first aspect relates to hygiene applications. The polymers according to the first aspect demonstrate a high absorbing and swelling capacity of organic solvents like ethanol, ethyl acetate, or dimethyl ketone. Hydrogels of organic solvents are used in disinfection products.

In at least one embodiment, the composition comprising a polymer according to the first aspect relates to oil field applications. Polymers according to the first aspect in oil field applications have to stand hostile environments and require thermal and hydrolytic stability and the resistance to hard water containing metal ions. For example, in drilling operations where conditions of high salinity, high temperature, and high pressure are present, these polymer can inhibit fluid loss and be used in oil field environments as scale inhibitors, pipeline flow improvers, as additives in refinery chemicals, friction reducers and water-control polymers, and in polymer flooding applications.

In at least one embodiment, the composition comprising a polymer according to the first aspect relates to water treatment applications. The cation stability of the ACDMT containing polymers are very useful for water treatment processes. Such polymers with low molecular weights cannot only inhibit calcium, magnesium, and silica scale in cooling towers and boilers, but also help corrosion control by dispersing iron oxide. When high molecular weight polymers are used, they can be used to precipitate solids in the treatment of industrial effluent stream.

In at least one embodiment, the composition comprising a polymer according to the first aspect relates to crop protection compositions. Polymers according to the first aspect increase, in dissolved and nanoparticulate polymer formulations, the bioavailability of pesticides in aqueous-organic formulations.

In at least one embodiment, the composition comprising a polymer according to the first aspect relates to membranes. Polymers according to the first aspect increase water flow, retention and fouling resistance of asymmetric ultrafiltration and microfiltration membranes and is being studied as an anionic component in polymer fuel cell membranes.

In at least one embodiment, the composition comprising a polymer according to the first aspect relates to construction applications. Polymers according to the first aspect can be used as superplasticizers to reduce water in concrete formulations. Benefits of these additives include improved strength, improved workability, improve durability of cement mixtures. Dispersible polymer powder, when bio based ACDMT is introduced, in cement mixtures control air pore content and prevent agglomeration of powders during the spray-drying process from the powder manufacturing and storage. Coating formulations with polymers according to the first aspect prevent calcium ions from being formed as lime on concrete surface and improve the appearance and durability of coating.

In at least one embodiment, the composition comprising a polymer according to the first aspect relates to a fire-fighting device-additive for the firegrade A. The liquid polymer—solution absorbs a multiple amount of its own weight in water and forms an adhesive and heat-shielding gel which contains no air bubbles but consists of evenly thickened water. The composition comprising a polymer according to the first aspect has a very good adhesive quality. It even sticks in thickness up to 10 mm at smooth, vertical surfaces (i.e. windows) or on ceilings.

In at least one embodiment, the composition comprising a polymer according to the first aspect relates to lubricant and fuel additives.

In at least one embodiment, the composition comprising a polymer according to the first aspect relates to driveline additives.

In at least one embodiment, the composition comprising a polymer according to the first aspect relates to engine oil additives.

In at least one embodiment, the composition comprising a polymer according to the first aspect relates to fuel additives.

In at least one embodiment, the composition comprising a polymer according to the first aspect relates to industrial lubricant additives.

In at least one embodiment, the composition comprising a polymer according to the first aspect can use for ion exchange resins.

EXAMPLES

The examples which follow are intended to illustrate the subject matter of the invention, without restricting it thereto.
Polymerization Process A:
General Precipitation Polymerization Procedure in Tert.-Butanol Dose in a 1-Liter Quickfit round bottom flask equipped with a reflux condenser, sub surface gas inlet tubing, inner temperature sensor and overhead agitator 400 g tert.-butanol with a water content of 2.5 wt.-%. Charge 100 g bio-based ACDMT according to the invention. Neutralize the ACDMT to a pH of 7 to 8 by injection of gaseous ammonia above the surface. Keep the temperature below 40° C. Dose a 1.45 g TMPTA as a crosslinker according to table A. Inject nitrogen subsurface for 1 h at agitation of 200 rpm. During this time the temperature of the reaction mixture is raised and stabilized to 60° C. with help of a water bath. Readjust the pH at 60° C. to a pH of 7 to 8. The reaction is initiated by the dosage of radical building compound, 1.3 g DLP.

After a few minutes the start of polymerization becomes obvious due to the rising temperature and the precipitation of a polymer. When the temperature maximum is reached, heat the reaction to a gentle reflux for two hours. Cool the reaction mixture to room temperature and dry the polymer suspension at 60° C. under a vacuum of 150 mbar.
Polymerization Process B:
General Precipitation Polymerization Procedure in Tert.-Butanol/Dimethylketone Mixture Dose in a 1-Liter Quickfit round bottom flask equipped with a reflux condenser, sub surface gas inlet tubing, inner temperature sensor and overhead agitator 200 g tert.-butanol and 200 g dimethylketone with a water content of 3 wt.-%. Charge 100 g bio-based ACDMT according to the invention. Neutralize the ACDMT by charging 40.5 g sodium hydrogen carbonate. Keep the temperature below 40° C. Dose 1.45 g TMPTA, as a crosslinker and according to table B. Inject nitrogen subsurface for 1 h at agitation of 200 rpm. During this time the temperature of the reaction mixture is raised and stabilized to 60° C. with help of a water bath. Readjust the pH at 60° C. to a pH of 7 to 8. The reaction is initiated by the dosage of radical building compound, 1.3 g DLP.

After a few minutes the start of polymerization becomes obvious due to the rising temperature and the precipitation of a polymer. When the temperature maximum is reached, heat the reaction to a gentle reflux for two hours. Cool the reaction mixture to room temperature and dry the polymer suspension at 60° C. under a vacuum of 150 mbar.

TABLE a

Polymers according to polymerization process A:

| | ACDMT | | | Crosslinker | | | Initiator | |
|---|---|---|---|---|---|---|---|---|
| Name | g | mol-% | Name | g | mol-% | Name | | g |
| Polymer-A 1 | 100.0 | 99.0 | TMPTA | 1.45 | 1.00 | DLP | | 1.30 |
| Polymer-A 2 | 100.0 | 98.7 | TMPTA | 1.81 | 1.25 | DLP | | 2.00 |

TABLE a-continued

Polymers according to polymerization process A:

| Name | ACDMT g | ACDMT mol-% | Crosslinker Name | Crosslinker g | Crosslinker mol-% | Initiator Name | Initiator g |
|---|---|---|---|---|---|---|---|
| Polymer-A 3 | 100.0 | 99.0 | TMPTA | 2.17 | 1.50 | DLP | 1.30 |
| Polymer-A 4 | 100.0 | 97.1 | TMPMTA | 4.50 | 2.94 | V-601 | 1.10 |
| Polymer-A 5 | 100.0 | 98.5 | TMPMTA | 2.30 | 1.52 | V-601 | 1.10 |
| Polymer-A 6 | 100.0 | 98.0 | TMPMTA | 3.05 | 2.01 | V-601 | 1.10 |
| Polymer-A 7 | 100.0 | 99.0 | PEG 600 DMA | 2.80 | 1.01 | V-601 | 1.10 |
| Polymer-A 8 | 100.0 | 98.5 | PEG 600 DMA | 4.25 | 1.52 | DLP | 2.00 |
| Polymer-A 9 | 100.0 | 98.8 | PEG 600 DMA | 3.48 | 1.25 | DLP | 2.00 |
| Polymer-A 10 | 100.0 | 97.0 | GPTA | 6.30 | 2.96 | V-601 | 1.10 |
| Polymer-A 11 | 100.0 | 98.0 | GPTA | 4.20 | 1.99 | V-601 | 1.10 |
| Polymer-A 12 | 100.0 | 98.8 | GPTA | 2.60 | 1.24 | V-601 | 1.10 |
| Polymer-A 13 | 100.0 | 99.0 | PEAS | 2.50 | 1.00 | V-601 | 1.10 |
| Polymer-A 14 | 100.0 | 98.5 | PEAS | 3.80 | 1.52 | V-601 | 1.10 |
| Polymer-A 15 | 100.0 | 98.8 | PEAS | 3.10 | 1.24 | V-601 | 1.10 |

ACDMT = acryloyldimethyltaurate, NVP = N-vinylpyrollidone, DMAAm = dimethylacrylamide, TMPTA = trimethylolpropantriacrylate, TMPTA = trimethylolpropane triacrylate, TMPTMA = trimethylolpropane trimethacrylate, GPTA = glycerin propoxylate triacrylate, PEAS = pentaerythritoldiacrylate monostearate, DLP = dilaurylperoxide, V-601 = dimethyl 2,2'-azobis(2-methylpropionate), polyethylene glycol dimethacrylate (600 g/mol).

TABLE b

Polymers according to polymerization process B:

| Name | ACDMT g | ACDMT mol-% | Neutralization reagent Name | Neutralization reagent g | Crosslinker Name | Crosslinker g | Crosslinker mol-% | Initiator Name | Initiator g |
|---|---|---|---|---|---|---|---|---|---|
| Polymer-B 1 | 100.0 | 99.0 | NaHCO$_3$ | 40.5 | TMPTA | 1.45 | 1.00 | DLP | 1.30 |
| Polymer-B 2 | 100.0 | 98.7 | NaHCO$_3$ | 40.5 | TMPTA | 1.81 | 1.25 | DLP | 2.00 |
| Polymer-B 3 | 100.0 | 98.5 | NaHCO$_3$ | 40.5 | TMPTA | 2.17 | 1.50 | DLP | 2.00 |
| Polymer-B 4 | 100.0 | 97.0 | KHCO$_3$ | 48 | TMPTA | 4.35 | 2.95 | V-601 | 1.10 |
| Polymer-B 5 | 100.0 | 97.0 | LiHCO$_3$ | 32.6 | TMPTA | 2.17 | 1.50 | V-601 | 1.10 |
| Polymer-B 6 | 100.0 | 99.0 | NaHCO$_3$ | 40.5 | TMPMTA | 1.50 | 1.00 | V-601 | 1.10 |
| Polymer-B 7 | 100.0 | 98.7 | NaHCO$_3$ | 40.5 | TMPMTA | 1.89 | 1.25 | V-601 | 1.10 |
| Polymer-B 8 | 100.0 | 98.5 | NaHCO$_3$ | 40.5 | TMPMTA | 2.30 | 1.52 | DLP | 2.00 |
| Polymer-B 9 | 100.0 | 98.5 | KHCO$_3$ | 48 | TMPMTA | 2.30 | 1.52 | DLP | 2.00 |
| Polymer-B 10 | 100.0 | 98.5 | LiHCO$_3$ | 32.6 | TMPMTA | 2.30 | 1.52 | DLP | 2.00 |
| Polymer-B 11 | 100.0 | 97.0 | LiHCO$_3$ | 32.6 | PEG 600 DMA | 8.50 | 3.00 | DLP | 2.00 |
| Polymer-B 12 | 100.0 | 98.0 | NaHCO$_3$ | 40.5 | PEG 600 DMA | 5.60 | 2.00 | DLP | 2.00 |
| Polymer-B 13 | 100.0 | 98.8 | NaHCO$_3$ | 40.5 | PEG 600 DMA | 3.48 | 1.25 | DLP | 2.00 |
| Polymer-B 14 | 100.0 | 98.8 | NaHCO$_3$ | 40.5 | PEG 600 DMA | 3.48 | 1.25 | DLP | 2.00 |
| Polymer-B 15 | 100.0 | 98.8 | NaHCO$_3$ | 40.5 | GPTA | 2.60 | 1.24 | V-601 | 1.10 |
| Polymer-B 16 | 100.0 | 99.0 | Na$_2$CO$_3$ | 25.5 | GPTA | 2.06 | 0.99 | DLP | 2.00 |
| Polymer-B 17 | 100.0 | 98.5 | NaHCO$_3$ | 40.5 | GPTA | 3.15 | 1.50 | V-601 | 1.10 |
| Polymer-B 18 | 100.0 | 98.8 | Na$_2$CO$_3$ | 25.5 | GPTA | 2.60 | 1.24 | V-601 | 1.10 |
| Polymer-B 19 | 100.0 | 97.0 | NaHCO$_3$ | 40.5 | PEAS | 7.60 | 2.99 | V-601 | 1.10 |
| Polymer-B 20 | 100.0 | 98.5 | NaHCO$_3$ | 40.5 | PEAS | 3.75 | 1.50 | V-601 | 1.10 |

ACDMT = acryloyldimethyltaurate, NVP = N-vinylpyrollidone, DMAAm = dimethylacrylamide, TMPTA = trimethylolpropane triacrylate, TMPTA = trimethylolpropane triacrylate, TMPTMA = trimethylolpropane trimethacrylate, GPTA = glycerin propoxylate triacrylate, PEAS = pentaerythritoldiacrylate monostearate, DLP = dilaurylperoxide, V-601 = dimethyl 2,2'-azobis(2-methylpropionate), polyethylene glycol dimethacrylate (600 g/mol).

Analytical Methods

Determination of the Fickenscher k-Value:

This method was used to determine the k-value of certain polymers according to DIN EN ISO 1628-1.

A k-value measurement was a way to indirectly analyze the molecular weight/size of a polymer. A comparatively higher K-value corresponds to a larger molecular weight/size as compared to a polymer with the same composition and made by the same process.

By measuring the measuring the pass-through time of a solvent ($t^0$) and the pass-through time of a polymer solution ($t^c$) through the capillary of an Ubbelhode viscometer the relative viscosity was determined.

$$Z = \frac{t_c}{t_0} = \frac{\eta_c}{\eta_0}$$

From the relative viscosity z the k-value can be calculated according to $$lgz = \left[\frac{75k^2}{1 + 150k \times c} + k\right] \times 1$$

In this case $$k = \frac{1{,}5lgz - 1 \pm \sqrt{1 + \left(\frac{2}{c} + 2 + 1{,}5lgz\right)1{,}5lgz}}{150 + 300c}$$

$k$-value = 1000 $k$

Here in it was defined:

$Z = \frac{t_c}{t_0} = \frac{\eta_c}{\eta_0}$ relative Viscosity, $\eta_c$     dynamic viscosity of the solution, $\eta_o$     dynamic viscosity of the solvent and $c_3$     mass concentration of polymer in solution in in g/cm.

Alternatively the k-value can be evaluated from lists provided by the manufacturer of the equipment.

After determination of the mass concentration of the polymer solution by microwave drying with a CEM Smart 5 at 120° C., 20 ml of a 0.5% polymer solution was prepared. 16 to 18 ml of the solution was measured in an Ubbelhode capillary viscometer at 25° C. The Ubbelhode viscometer was chose to have a pass-through time of 100 to 120 s. It was measured in a Schott AVS viscometer, combined with a CT 1150 Thermostate and flow cooler CK 100.

The IT unit calculated the k-value.

Brookfield Viscosity in 1% Solution:

Brookfield viscosity was determined with a Brookfield viscometer model LV, RVT DV-II or LVT DV-II.

In a 600 ml beaker, 4 g dry Polymer was dissolved in 394 g distilled water. The solution was stirred for 2 h at 20° C. with a finger stirrer driven by an overhead agitator at 200 rpm. Then the polymer solution, free of entrapped air, was tempered for 16 h at 20° C. The spindle was chosen to measure between 20 to 80% of the scale at 20 rpm.

Brookfield viscosity in solution as is.

Brookfield viscosity was determined with a Brookfield viscometer model LV, RVT DV-II or LVT DV-II.

In a 600 ml beaker, the polymer solution, free of entrapped air, was tempered for 2 h at 20° C. The spindle was chosen to measure between 20 to 80% of the scale at 20 rpm.

Analytical procedure for determination of bio-based content according to ASTM 6866-12, Method B:

The provided sample material did not undergo any pre-treatment procedure and was converted to graphite as was using the following procedure.

Depending on the estimated amount of carbon content, typically a few milligram of sample material was being combusted in an Elemental Analyzer (EA). The resulting gas mixture was being cleaned and $CO_2$ was automatically separated by the EA using the purge and trap technology.

The remaining $CO_2$ was transferred into a custom-made graphitization system, converted into carbon (graphite) catalytically using $H_2$ and an iron-powder catalyst.

The carbon-14 determination of the graphite was performed at the Klaus-Tschira-Archaeomtrie-Center using an accelerator mass-spectrometer (AMS) of the type MICADAS (developed at the ETH Zurich, Switzerland).

EXPERIMENTAL

Experimental Example 1: Polymers According to Polymerization Process B Viscosity Dependence on Polymer Concentration The following example comprises a polymer according to the present invention as Polymer-B 16 compared with Polymer-B 16 #. Polymer-B 16 # being a comparative example in that is the same as Polymer-B 16 but with common building blocks derived from petrochemicals.

See FIG. 1: The viscosity measurements in dependence of polymer concentration with Polymer-B 6 (solid line) and Polymer-B 16 # (broken line) showed very similar results, therefore Polymer-B 16 and Polymer-B 16 # are interchangeable with one another.

Experimental Example 2: Polymers According to Polymerization Process B: Viscosity Dependence on pH The following example comprises a polymer according to the present invention as Polymer-B 16 compared with Polymer-B 16 #. Polymer-B 16 # being a comparative example in that is the same as Polymer-B 16 but with common building blocks derived from petrochemicals.

Figure 2:
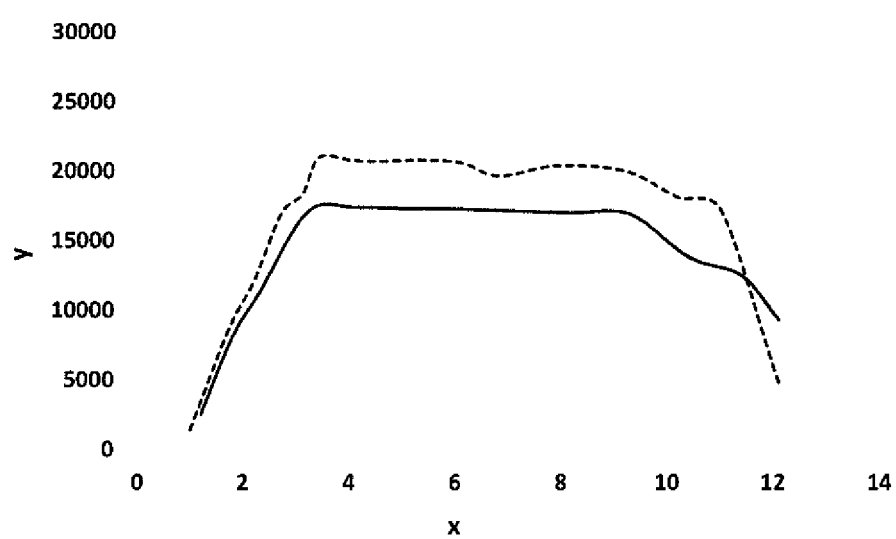
FIG. 2: Viscosity dependence on pH; 1.0 wt. % polymer measured in deionized water (Brookfield RVDV-1, 20° C., 20 rpm). The x-axis shows the pH. The y-axis shows the viscosity in mPa·s. Polymer-B 16 (according to the invention; solid line) and a comparative polymer-B 16 # are compared (broken line).

See FIG. 2: The viscosity measurements and their dependence on pH with Polymer-B 16 and Polymer-B 16 # showed very similar results, therefore Polymer-B 16 and Polymer-B 16 # are interchangeable with one another.

Experimental Example 3: Polymers According to Polymerization Process A: Viscosity Dependence on pH The following example comprises a polymer according to the present invention as Polymer-A 2 compared with Polymer-A 2 #. Polymer-A 2 # being a comparative example in that is the same as Polymer-A 2 but with common building blocks derived from petrochemicals.

Figure 3:
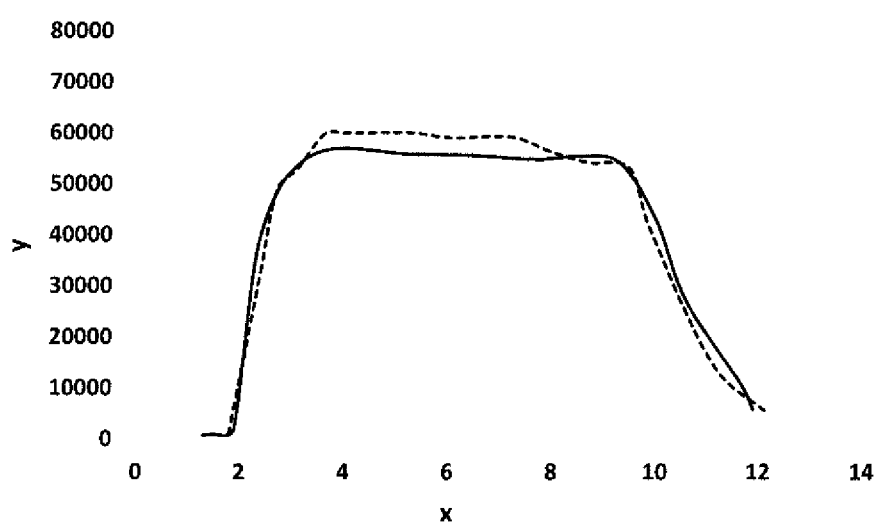
FIG. 3: Viscosity dependence on pH; 1.0 wt. % polymer measured in deionized water (Brookfield RVDV-1, 20° C., 20 rpm). The x-axis shows the pH. The y-axis shows the viscosity in mPa·s. Polymer-A 2 (according to the invention; solid line) and a comparative polymer-A 2 # are compared (broken line).

See FIG. 3: The viscosity measurements and their dependence on pH with Polymer-A 2 and Polymer-A 2 # showed very similar results, therefore Polymer-A 2 and Polymer-A 2 # are interchangeable with one another.

EXAMPLE COMPOSITIONS (ACCORDING TO THE FOURTH ASPECT)

Example Composition 1: Effect Shower Gel pH=5.0, 510 mPa·s (Brookfield RVDV-1, 20° C., 20 rpm, S04)

| | | |
|---|---|---|
| A | Genapol ® LRO liquid (Clariant) Sodium Laureth Sulfate | 30.00% |
| | Genagen ® CAB 818 (Clariant) Cocamidopropyl Betaine | 6.00% |
| | Hostapon ® KCG (Clariant) Sodium Cocoyl Glutamate | 5.00% |
| B | Water | Ad 100% |
| C | Polymer-A 2 (according to polymerization process A) | 1.40% |
| D | Nipaguard ® DMDMH (Clariant) DMDM Hydantoin | 0.50% |
| | Cirebelle 104 Blue Synthetic Wax | 1.00% |

Procedure

I Mix components of A and B until complete dissolved.

II Add C and stir until the solution is free of lumps.

III Add D to II.

IV Finally adjust the pH if necessary to 5.5-6.5.

Example Composition 2: O/W Foundation pH=6.0, 18 650 mPa·s (Brookfield RVDV-1, 20° C., 20 rpm, S06)

| A | Water | Ad 100% |
|---|---|---|
|   | Polymer-A 2 | 1.00% |
|   | (according to polymerization process A) | |
|   | Magnesium Aluminium Silicate | 1.00% |
| B | Plantasens ® Natural Emulsifier HP10 (Clariant) | 4.50% |
|   | Sucrose Polystearate, Cetearyl Alcohol, *Olea Europaea* (Olive) Oil Unsaponifiables | |
|   | SilCare ® Silicone 31M50 (Clariant) | 2.00% |
|   | Caprylyl Trimethicone | |
|   | XIAMETER ® PMX-200 Silicone Fluid 100 CS | 2.00% |
|   | Dimethicone | |
|   | Caprylic/Capric Triglyceride | 5.00% |
|   | Plantasens ® Olive Wax S51 (Clariant) | 1.50% |
|   | Hydrogenated Vegetable Oil | |
| C | Chroma-Lite ® Black | 0.10% |
|   | Mica (and) Bismuth Oxychloride (and) Iron Oxides | |
|   | Chroma-Lite ® Red | 0.40% |
|   | Mica (and) Bismuth Oxychloride (and) Iron Oxides | |
|   | Chroma-Lite ® Yellow | 1.20% |
|   | Mica (and) Bismuth Oxychloride (and) Iron Oxides | |
|   | Titanium Dioxide | 7.00% |
|   | Dicaprylyl Carbonate | 4.00% |
|   | Butylene Glycol | 3.00% |
| D | Plantasens ® Natural Vitamin E (Clariant) | 1.00% |
|   | Tocopherol | |
|   | Orgasol ® 4000 EXD NAT COS Caresse | 1.00% |
|   | Nylon-6/12 | |
|   | Fragrance | 0.20% |
|   | Nipaguard ® POB (Clariant) | 0.80% |
|   | Phenoxyethanol (and) Piroctone Olamine (and) Benzoic Acid | |

Procedure
I Mix ingredients of phase A and homogenize gently by using Ultra-Turrax, then stir and heat to 70° C.
II Mix ingredients of phase B and heat to 70° C.
III Premix phase C then add to B and homogenize gently by using Ultra-Turrax.
IV Pour III into I and homogenize gently by using Ultra-Turrax. Then stir until 35° C.
V Add phase D and stir until homogeneous.
VI Adjust the pH to 5.5 to 6.0 if necessary.

Example Composition 3: Anti-Ageing Cream Gel pH=5.1, 1580 mPa·s (Brookfield RVDV-1, 20° C., 20 rpm, S04)

| A | Caprylic/Capric Triglyceride | 5.00% |
|---|---|---|
|   | Dicaprylyl Ether | 5.00% |
|   | Cetearyl Alcohol | 2.00% |
|   | Nipaguard ® POB (Clariant) | 0.80% |
|   | Phenoxyethanol (and) Piroctone Olamine (and) Benzoic Acid | |
| B | Ubiquinone | 0.10% |
| C | Aristoflex ® HMB (Clariant) | 0.40% |
|   | Ammonium Acryoyldimethyltaurate/ Beheneth-25 Methacrylate Crosspolymer | |
|   | Polymer-A 2 | 0.40% |
|   | (according to polymerization process A) | |
| D | Sodium Hyaluronate | 0.30% |
| E | Water | Ad 100% |
| F | Tocopheryl Acetate | 0.30% |
|   | Fragrance | 0.30% |

Procedure
I Mix components of A and melt at 60° C.
II Add B and solve while shaking lightly.
III Add C.
IV Solve D in E and add to III.
V Add F to IV at 35° C.
VI Finally adjust the pH if necessary to 5.0-6.0.

Example Composition 4: Caring Night Cream pH=5.8, 22 450 mPa·s (Brookfield RVDV-1, 20° C., 20 rpm, S06)

| A | Water | Ad 100% |
|---|---|---|
|   | Glycerin | 2.00% |
|   | Polymer-A 2 | 1.00% |
|   | (according to polymerization process A) | |
| B | Hostaphat ® KW 340 D (Clariant) | 2.00% |
|   | Triceteareth-4 Phosphate | |
|   | Plantasens ® Oat Serum (Clariant) | 3.00% |
|   | *Avena Sativa* (Oat) Kernel Oil (and) Phytosterols (and) *Olea Europaea* (Olive) Oil Unsaponifiables (and) Beeswax | |
|   | Plantasens ® Shea Butter (Clariant) | 7.00% |
|   | *Butyrospermum Parkii* (Shea) Butter | |
|   | Isopropyl Palmitate | 5.00% |
|   | *Macadamia Integrifolia* Seed Oil | 4.00% |
|   | Cera Alba (Beeswax) | 3.00% |
| C | Nipaguard ® SCP (Clariant) | 1.00% |
|   | Phenoxyethanol (and) Sorbitan Caprylate | |
|   | Fragrance | 0.30% |
| D | Sodium Hydroxide | 0.10% |

Procedure
I Mix ingredients of phase A and heat to 75° C.
II Mix ingredients of phase B and heat to 75° C.
III Pour phase B into phase A and homogenize gently.
IV Cool down under stirring.
V Below 40° C. add C and stir.
VI Adjust pH with D to 5.5-6.5.

Example Composition 5: Hand Sanitizer pH=5.4, 30 600 mPa·s (Brookfield RVDV-1, 20° C., 20 rpm, S06)

| A | Water | ad 100% |
|---|---|---|
|   | Glycerin | 2.00% |
|   | Polymer-A 2 | 0.50% |
|   | (according to polymerization process A) | |
| B | Ethanol | 70.0% |
|   | XIAMETER ® OFX-5324 Fluid | 6.00% |
|   | PEG-12 Dimethicone | |
|   | *Aloe Barbadensis* Leaf Extract | 0.30% |

Procedure
I Mix components of A until a homogeneous gel is formed.
II Add B to A and stir until homogeneous.

Alternatives to composition examples 1 to 5 include where any of the Polymers B 1 to B 20 or Polymer-A 1 or Polymers A 3 to A 15 (see above tables) are used in instead of Polymer A 2.

The invention claimed is:
1. A polymer comprising:
(a) from 90 mol-% to 99.9 mol-% of repeating units according to Formula (1), wherein at least 10 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B, calculated by multiplying percent modern carbon value, as determined by measuring carbon-14 content relative to total carbon content, by a correction factor of 0.95;

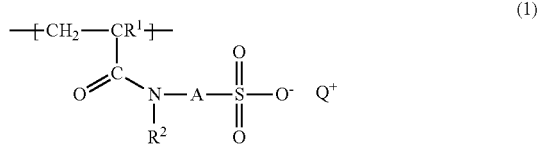

wherein:
- $R^1$ and $R^2$ are independently selected from group consisting of H, methyl and ethyl; A is a linear or branched $C_1$-$C_{12}$-alkyl group; and $Q^+$ is $H^+$, $NH_4^+$, organic ammonium ions $[NHR^5R^6R^7]^+$ wherein $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$, ⅓ $Al^{+++}$, or combinations thereof; and
- (b) from 0.01 mol-% to 10 mol-% of crosslinking or branching units, wherein the crosslinking or branching units result from the incorporation of a monomer comprising at least two olefinically unsaturated double bonds.

2. The polymer according to claim 1, wherein at least 25 wt.-% of the repeating units (a) according to Formula (1) comprise from 28 wt.-% to 100 wt.-% bio-based carbon content, relative to the total mass of carbon in the repeating unit according to Formula (1), measured according to standard ASTM D6866-12, Method B, calculated by multiplying percent modern carbon value, as determined by measuring carbon-14 content relative to total carbon content, by a correction factor of 0.95.

3. The polymer according to claim 1, any of claims 1 to 2, wherein the repeating unit (a) according to Formula (1) comprises from 35 wt.-% bio-based carbon content, relative to the total mass of carbon in the repeating unit (a) according to Formula (1), measured according to standard ASTM D6866-12, Method B, calculated by multiplying percent modern carbon value, as determined by measuring carbon-14 content relative to total carbon content, by a correction factor of 0.95.

4. The polymer according to claim 1, wherein the repeating units (a) according to Formula (1) have a degree of neutralisation of from 50.0 to 100 mol-%.

5. The polymer according to claim 1, wherein the polymer comprises at least one repeating unit (a) according to Formula (1), wherein $R^1$ and $R^2$ are independently selected from the group consisting of H, methyl and ethyl; A is a linear or branched $C_1$-$C_{12}$-alkyl group; and $Q^+$ is $H^+$, $Li^+$, $Na^+$, $K^+$, ½ $Ca^{++}$, ½ $Mg^{++}$, ½ $Zn^{++}$, ⅓ $Al^{+++}$, or combinations thereof.

6. The polymer according to claim 1, wherein the polymer comprises from 95 mol-% to 99.9 mol-% of repeating units (a) according to Formula (1).

7. The polymer according to claim 1, wherein the repeating units (a) according to Formula (1) result from the incorporation of a monomer selected from the group consisting of acryloyldimethyltaurates, acryloyl-1,1-dimethyl-2-methyltaurates, acryloyltaurates, acryloyl-N-methyltaurates, and combinations thereof.

8. The polymer according to claim 7, wherein the acryloyldimethyltaurate comprises from 35 wt.-% bio-based carbon content, relative to the total mass of carbon in the acryloyldimethyltaurate, measured according to standard ASTM D6866-12, Method B, calculated by multiplying percent modern carbon value, as determined by measuring carbon-14 content relative to total carbon content, by a correction factor of 0.95.

9. The polymer according to claim 1, wherein the crosslinking or branching units result from the incorporation of a monomer according to Formula (4)

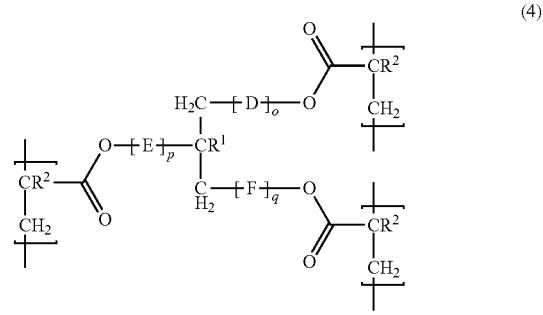

wherein
- $R^1$ is independently selected from the group consisting of H, methyl and ethyl; and
- $R^2$ is a linear or branched alkyl group having 1 to 6 carbon atoms, or is a linear or branched, mono- or polyunsaturated alkylene group having 2 to 6 carbon atoms;
- D, E, and F are independently methyleneoxy($-CH_2O$), ethyleneoxy($-CH_2-CH_2-O-$), propyleneoxy($-CH(CH_3)-CH_2-O-$), a linear or branched alkylene group having 1 to 6 carbon atoms, a linear or branched, singularly or multiply unsaturated alkenylene group having 2 to 6 carbon atoms, a linear mono-hydroxyalkylene group having 2 to 6 carbon atoms or a linear or branched dihydroxyalkylene group having 3 to 6 carbon atoms; and
- o, p, and q each independently are an integer from 1 to 50.

10. The polymer according to claim 1, wherein the crosslinking or branching units (b) result from the incorporation of a crosslinker selected from the group consisting of trimethylolpropane triacrylatee (TMPTA), glycerol propoxylate triacrylate (GPTA), and mixtures thereof.

11. The polymer according to claim 1, wherein the polymer consists of:
(a) from 90 mol-% to 99.9 mol-% repeating units according to Formula (1) wherein at least 10 wt.-% of the repeating units according to Formula (1) comprise from 28 wt.-% to 100 wt.-% bio-based carbon content, relative to the total mass of carbon in the repeating unit according to Formula (1), measured according to standard ASTM D6866-12, Method B, calculated by multiplying percent modern carbon value, as determined by measuring carbon-14 content relative to total carbon content, by a correction factor of 0.95;

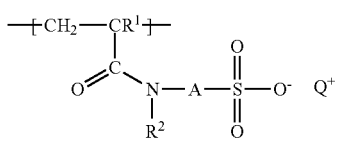

wherein:

$R^1$ and $R^2$ are independently selected from the group consisting of H, methyl and ethyl; A is a linear or branched $C_1$-$C_{12}$-alkyl group; and $Q^+$ is $H^+$, $NH_4^+$, organic ammonium ions $[NHR^5R^6R^7]^+$ wherein $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$, ⅓ $Al^{+++}$, or combinations thereof; and (b) from 0.01 mol-% to 10 mol-% crosslinking or branching units, wherein the crosslinking or branching units result from the incorporation of a monomer comprising at least two olefinically unsaturated double bonds.

12. The polymer according to claim 1, wherein the polymer has a weight average molecular weight of at least 700 g/mol.

13. The polymer according to claim 1, wherein at least 20 wt.-% of the repeating units (a) according to Formula (1) comprise from 35 wt.-% bio-based carbon content, relative to the total mass of carbon in the repeating unit (a) according to Formula (1), measured according to standard ASTM D6866-12, Method B, calculated by multiplying percent modern carbon value, as determined by measuring carbon-14 content relative to total carbon content, by a correction factor of 0.95.

14. The polymer according to claim 1, wherein at least 25 wt.-% of the repeating units (a) according to Formula (1) comprise about 100 wt.-% bio-based carbon content, relative to the total mass of carbon in the repeating unit (a) according to Formula (1), measured according to standard ASTM D6866-12, Method B, calculated by multiplying percent modern carbon value, as determined by measuring carbon-14 content relative to total carbon content, by a correction factor of 0.95.

15. The polymer according to claim 1, wherein the repeating units (a) according to Formula (1) result from the incorporation of an acryloyldimethyltaurate.

16. The polymer according to claim 1, wherein
the repeating units (a) according to Formula (1) result from the incorporation of a acryloyldimethyltaurate; and
at least 20 wt.-% of the repeating units (a) according to Formula (1) comprise from 35 wt.-% bio-based carbon content, relative to the total mass of carbon in the repeating unit (a) according to Formula (1), measured according to standard ASTM D6866-12, Method B, calculated by multiplying percent modern carbon value, as determined by measuring carbon-14 content relative to total carbon content, by a correction factor of 0.95.

17. The polymer according to claim 1, wherein the polymer has a weight average molecular weight of from 700 g/mol to 10 million g/mol.

18. A process for preparing a polymer comprising the step of polymerizing: (a) at least one monomer according to Formula (10) comprising from 28 wt.-% to 100 wt.-% bio-based carbon content, relative to the total mass of carbon in the monomer according to Formula (10), measured according to standard ASTM D6866-12, Method B; calculated by multiplying percent modern carbon vlaue, as determined by measuring carbon-14 content relative to total carbon content, by a correction factor of 0.95; (b) at least one crosslinking or branching monomer; (c) optionally at least one neutral monomer; and (d) optionally at least one anionic monomer;
wherein the crosslinking or branching monomer has at least two olefinically unsaturated double bonds;
and wherein Formula (10) is:

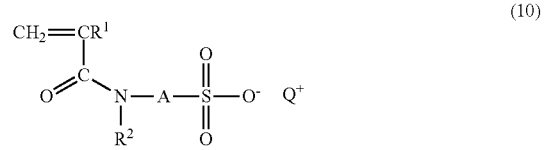

wherein:

$R^1$ and $R^2$ are independently selected from H, methyl or ethyl; A is a linear or branched $C_1$-$C_{12}$-alkyl group; and $Q^+$ is $H^+$, $NH_4^+$, organic ammonium ions $[NHR^5R^6R^7]^+$ wherein $R^5$, $R^6$, and $R^7$ independently of one another may be hydrogen, a linear or branched alkyl group having 1 to 22 carbon atoms, a linear or branched, singularly or multiply unsaturated alkenyl group having 2 to 22 carbon atoms, a $C_6$-$C_{22}$ alkylamidopropyl group, a linear mono-hydroxyalkyl group having 2 to carbon atoms or a linear or branched dihydroxyalkyl group having 3 to carbon atoms, and where at least one of the radicals $R^5$, $R^6$, and $R^7$ is not hydrogen, or $Q^+$ is $Li^+$, $Na^+$, $K^+$, ½ $Ca^{++}$, ½ $Mg^{++}$, ½ $Zn^{++}$, ⅓ $Al^{+++}$, or combinations thereof.

19. A method for thickening a composition, or for modifying a rheology or viscosity of the composition, comprising the step of adding at least one polymer according to claim 1 to the composition.

20. A composition comprising:
(a) at least one polymer according to claim 1, and
(b) at least one further component.

* * * * *